(12) United States Patent
Donovan

(10) Patent No.: US 9,545,431 B1
(45) Date of Patent: Jan. 17, 2017

(54) ISOLATED RECOMBINANT CDNA

(75) Inventor: David M. Donovan, Baltimore, MD (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 1080 days.

(21) Appl. No.: 12/470,321

(22) Filed: May 21, 2009

Related U.S. Application Data

(60) Provisional application No. 61/128,713, filed on May 23, 2008.

(51) Int. Cl.
*A61K 38/00* (2006.01)

(52) U.S. Cl.
CPC .................................... *A61K 38/00* (2013.01)

(58) Field of Classification Search
None
See application file for complete search history.

(56) References Cited

FOREIGN PATENT DOCUMENTS

WO    WO/0234771    *  5/2002

OTHER PUBLICATIONS

Donovan et al. (FEMS Microbiology Letters, vol. 287 (1), pp. 22-33, 2008).*

* cited by examiner

*Primary Examiner* — Hope Robinson
(74) *Attorney, Agent, or Firm* — John D. Fado; Evelyn M. Rabin

(57) ABSTRACT

The routine use of antibiotics to battle Streptococcal pathogens has produced a new class of superbug—multi-drug resistant streptococci resulting in a need for new antimicrobials. The LambdaSa2 prophage endolysin gene harbors an amidase-5 (endopeptidase), an amidase-4 (glycosidase) domain and two Cpl-7 cell wall-binding domains. This endolysin can digest the cell walls of *Streptococcus agalactiae, Streptococcus pneumoniae* and *Staphylococcus aureus*. Turbidity reduction and plate lysis assays indicate that this peptidoglycan hydrolase also shows strong lytic activity toward *Streptococcus pyogenes, Streptococcus dysgalactiae, Streptococcus uberis, Streptococcus equi*, GES, and GGS. Deletion analysis on the His-tagged version of this gene further indicates that the N-terminal endopeptidase domain is minimally active in the absence of a Cpl-7 domain when lysing cells from without; however, with both Cpl-7 domains, it achieves a higher specific activity than the full length protein (on some strains) and shows weak activity against two Coagulase Negative Staphylococci, *Staphylococcus hyicus* and *Staphylococcus xyloses*.

12 Claims, 9 Drawing Sheets

ISOLATED RECOMBINANT cDNA

REFERENCE TO RELATED APPLICATION

This application claims the benefit of U.S. Provisional Application No. 61/128,713, filed May 23, 2008, which is incorporated herein by reference in its entirety.

BACKGROUND OF THE INVENTION

Field of the Invention

This invention relates to a nucleic acid encoding a functional module or domain of a particular peptidoglycan hydrolase, the streptococcal phage λSa2 endolysin, a protein which digests the peptidoglycan cell wall of streptococcal species with near species-specificity. Optimal $Ca^{++}$ and NaCl concentrations and pH have been determined for native λSa2 endolysin and for multiple truncations of λSa2 endolysin. The invention further relates to lysis of untreated, live streptococcal bacteria observed as a result of native and truncated λSa2 lysis activity and enhancement of that activity on streptococcal bacteria as well as staphylococcal bacteria when the nucleic acid encoding the functional endopeptidase domain is further modified with one or more copies of endogenous phage cell wall-binding domains, i.e., Cpl-7 domains or with the SH3b cell wall-binding domain from the bacteriocin lysostaphin. The invention further relates to compositions and methods of treating diseases caused by the bacteria for which the λSa2 endopeptidase and modified λSa2 endopeptidase are specific, namely, streptococcal diseases, and in addition, compositions and methods comprising λSa2 endopeptidase for treating staphylococcal-associated diseases, including methicillin-resistant *Staphylococcus aureus* (MRSA).

Description of the Relevant Art

Streptococci are notorious pathogens in animals and man, with *S. pneumoniae* being most widely recognized for the pneumonia it causes (2007. *Morb. Mortal. Wkly. Rep.* 56:1077-1080). Other streptococci are renowned, for example, for human diseases such as group A *streptococcus* (GAS) pharyngo-tonsillitis (Passali et al. 2007. *Acta Otorhinolaryngol. Ital.* 27:27-32), group C *streptococcus* (GCS)-associated wound infections, otitis media, purulent pharyngitis, and streptococcal toxic shock syndrome (Davies et al. 2007. *Clin. Infect. Dis.* 44:1442-1454; Salata et al. 1989. *Medicine* (Baltimore) 68: 225-239), and group G *streptococcus* (GGS)-associated bacteremia (Sylvetsky et al. 2002. *Am. J. Med.* 112:622-626). Similarly, for the animal diseases, examples are: GCS *Streptococcus equi* subsp. *zooepidemicus* of haemorrhagic pneumonia in dogs (Kim et al. 2007. *Vet. Rec.* 161: 528-530), and (GES) group E streptococcal lymphadenitis of swine (Wessman, G. E. 1986. *Vet. Microbiol.* 12: 297-328). Streptococci having the ability to infect both humans and livestock occur as well, as is seen in group B *streptococcus* (GBS) mastitis (Wilson et al. 1997. *J. Dairy Sci.* 80: 2592-2598), perinatal GBS disease of infants (2007. *Morb. Mortal. Wkly. Rep.* 56:701-705), and in *S. suis* causing septicemia, meningitis, endocarditis and arthritis in pigs and causing fever, malaise, nausea and vomiting, followed by nervous symptoms, subcutaneous hemorrhage, septic shock and coma in humans (Gottschalk et al. 2007. *Anim. Health Res. Rev.* 8:29-45). The streptococci are following the trend of all antibiotic-treated pathogens with high levels of antibiotic resistance development being noted by clinicians (2007. *Moth. Mortal. Wkly. Rep.* 56:1077-1080; Niederman, M. S. 2007. *Chest.* 131:1205-1215; Passali et al., supra) and veterinarians (Lloyd, D. H. 2007. *Clin. Infect. Dis.* 45 (Suppl. 2):S148-52; Mathew et al. 2007. *Foodbome Patholog. Dis.* 4:115-133).

In this age of increasing resistance to antibiotics, efforts to find novel antimicrobials are turning to bactericidal proteins of bacterial and/or phage origin (Hermoso et al. 2007. *Curr. Opin. Microbiol.* 10: 461-472). Many Gram positive bacteriophage endolysins have been tested and shown to be efficacious when exposed externally to host-related pathogens (lysis from without or exolysis) (for recent reviews, see Loessner, M. J. 2005. *Curr. Opin. Microbiol.* 8:480-487; Fischetti, V. A. 2005. *Trends Microbiol.* 13: 491-496). In fact, lysostaphin (a bacteriocin secreted by *Staphylococcus simulans* to kill *S. aureus*) recently achieved higher efficacy than vancomycin against clinical isolates of multi-drug resistant *Staphylococcus aureus* (Yang et al. 2007. *J. Med. Microbiol.* 56: 71-76).

In the search for new antimicrobials, it has been deemed essential by FDA, CDC, USDA and other US government agencies in an interagency forum to develop agents that avoid resistance Retrieved from the Internet: <URL: cdc.gov/drugresistance/actionplan/2005report/index.htm. In support of this federal objective, the near-species specificity of bacteriophage endolysins is anticipated to help avoid resistance development among the non-related commensal bacteria that are inadvertently exposed to antimicrobials, something that occurs routinely during antibiotic treatment episodes. Furthermore, for the few bacteriophage endolysins tested, no resistant strain development has been identified (reviewed in Fischetti, supra). In addition, the efficacy of peptidoglycan hydrolases as an antimicrobial agent has been demonstrated in animal models of human disease (Cheng at al. 2005. *Antimicrob. Agents Chemother.* 49:111-117; Entenza et al. 2005. *Antimicrob. Agents Chemother.* 49:4789-4792; Rashel et al. 2007. *J. Infect. Dis.* 196:1237-1247) as well as in animal disease applications e.g. transgenic cattle with mammary expression of lysostaphin have been shown to be resistant to *S. aureus*-induced mastitis (Wall et al. 2005. *Nat. Biotechnol.* 23: 445-451).

Most Gram Positive lysins (bacterial or, phage origin) have an N-terminal lytic domain and a C-terminal cell wall-binding domain. The lytic domain of the phage endolysin can have any of three functions: an amidase activity, an endopeptidase, or a lysozyme-like glycosidase activity. The cell wall bonds sensitive to amidase (N-acetylmuramyl-L-alanine) and glycosidase lysin activities (β-1,4-linked N-acetylglucosamine and N-acetyl muramic acid residues) are conserved in the peptidoglycan of nearly all bacterial species, while the amino acid sequence of the peptide portion of peptidoglycan that is sensitive to endopeptidase activity can vary between species and genera (Schleifer and Kandler. 1972. *Bacteria Rev.* 36: 407-477).

The stem peptide region of peptidoglycan is often conserved across multiple species, within any given genus. Species-specificity in peptidoglycan structure usually occurs in the interpeptide bridge (Schleifer and Kandler, supra). The result is that phage lysins that recognize and cleave bonds in the regions of the peptidoglycan that are conserved within a genus will often lyse a much broader range of species than just the host range of their phage of origin. For example, the streptococcal B30 bacteriophage is hosted by a relatively small subgroup of type III GBS, but the B30 phage lysin can kill streptococci of Lancefield groups A, B, C, E, and G, with the rate of lysis for groups A, C and G being much higher than the host GBS (Pritchard at al. 2004. *Microbiology* 150: 2079-2087).

Species-specificity of these lysins can originate in part from both the lytic and cell wall-binding domains. The species-specificity of lysin endopeptidase domains can easily be ascribed to the differences in amino acid sequences of the peptidoglycan. This has been demonstrated experimentally, with digestion of short synthetic peptides that mimic the bonds recognized by the endopeptidase domain in question (Pritchard et al. 2007. *Appl. Environ. Microbiol.* 73: 7150-7154). The bonds cleaved by amidase and glycosidase activities of lysins are so highly conserved among all bacterial species that it is difficult to imagine how these structures themselves confer specificity to the lysins. However, it is known that O-acetylation at the C6-OH of the N-acetylmuramic acid can affect lysozyme's ability to digest the sugar backbone (Bera et al. 2006. *Infect. Immun.* 74: 4598-4604), with only a few enzymes known with the ability to cleave this O-acetylated sugar backbone. (Pritchard et al. 2007, supra; Yokogawa et al. 1974. *Antimicrob. Agents Chemother.* 6:156-165). That being said, there are still other largely undefined factors that contribute to species-specificity of the lysins. A hint at one source of this specificity is apparent when it was reported that the B30 endolysin with an inactivated endopeptidase domain resulting from a site-directed mutation and an active Acm lysozyme-like domain could digest the prepared peptidoglycan of GBS (Pritchard et al. 2004, supra), but the same lysin could not lyse GBS as a growing cell (Donovan et al. 2006b. *Appl. Environ. Microbiol.* 72:5108-5112). These results suggest that non-peptidoglycan factors (i.e. present on growing cells, but not prepared peptidoglycan) can alter peptidoglycan sensitivity to the lysin. There are numerous other structures on the Gram Positive cell wall that might participate in defining peptidoglycan hydrolase specificity, e.g. teichoic acid, capsule, poly-N-acetylglucosamine. Their potential role in endolysin specificity is undefined.

The C-terminal cell wall-binding domain of peptidoglycan hydrolase enzymes is known to effect cell-type specificity. The SH3b domain of the staphylococcal lytic enzyme ALE-1 (which is virtually identical to the SH3b domain of lysostaphin) has been examined via both mutagenesis and crystallography (Lu et al. 2006b. *J. Biol. Chem.* 281: 549-558). This and other studies (Grundling and Schneewind. 2006. *J. Bacterial.* 188: 2463-2472) have indicated that the SH3b domain recognizes the penta-glycine interpeptide bridge of staphylococcal peptidoglycan. Prior studies have indicated that lysostaphin requires the C-terminal 92 amino acids, including the SH3b domain, for cell-type specificity (Baba and Schneewind. 1996. *EMBO J.* 15:4789-4797). Similarly, the SH3b domain of the PlyB endolysin from a *Bacillus anthrasis* phage is required for high levels of activity (Porter et al. 2007. *J. Mol. Biol.* 366: 540-550). Essential choline-binding domains that are specific for streptococcal cell walls have also been described (Garcia et al. 1990. *Gene* 86: 81-88; Sanchez-Puelles et al. 1990. *Gene* 89: 69-75) with the CPL-1 lysin harboring one such domain having been recently crystallized (Perez-Dorado at al. 2007. *J. Biol. Chem.* 282:24990-24999). Again, this endolysin demonstrates an absolute need for the choline-binding domain for lytic activity (see a recent review of those lysins which have been crystallized with cell wall-binding domains, Koehl et al. 2004. *Antimicrob. Agents Chemother.* 48: 3749-3757).

Despite an absolute requirement of a cell wall-binding domain for the full lytic activity of some lysins, numerous examples of higher activity from truncated endolysins lacking their SH3b domains have been reported, e.g., staphylococcal phage Twort (Loessner et al. 1998. *FEMS Microbiol. Lett.* 162:265-274) and phiWMY endolysins (Yokoi et al. 2005. *Gene* 351: 97-108), streptococcal phage endolysin PlyGBS (Cheng and Fischetti. 2007. *Appl. Microbiol. Biotechnol.* 74:1284-1291), and streptococcal B30 endolysin (Donovan at al. 2006. *Appl. Environ. Microbiol.* 72(7):5108-5112; Donovan at al. 2006. *Appl. Environ. Microbiol.* 72(4): 2988-96); *Bacillus anthrasis* Lambda phage endolysin PlyL lambda (Low at al. 2005. *J. Biol. Chem.* 280:35433-35439). This apparent inconsistency is further complicated by the fact that some lytic domains are not only more active, but maintain their cell type specificity in the absence of their SH3b cell wall-binding domain (Donovan et al. 2006b, supra). Still other domains do not show any activity toward their growing host when exposed externally (Donovan et al. 2007, supra) despite evidence that the domain is active on prepared peptidoglycan (Pritchard et al. 2004, supra). These inconsistent results dictate that a thorough analysis is needed of candidate peptidoglycan hydrolase antimicrobials to identify the most active domains and the constructs required to achieve lytic activity.

To counter the rise of drug resistant pathogenic bacteria, there is a need for new specific antimicrobial treatments. Reagents shown to be very specific for the genera, species or substrains of concern would give better effective control of economically important diseases and therefore are ideal candidates for therapeutic treatments. In this study we have identified the domains necessary for lysis from without (exolysis) for the Lambda Sa2 endolysin (λSa2), identified constructs that enhance the native enzyme activity level against the target species, (streptococcal), and extended the list of pathogen species known to be lysed by the enzyme.

SUMMARY OF THE INVENTION

We have discovered the nucleic acid encoding the λSa2 endolysin, a protein which specifically attacks the peptidoglycan cell wall of untreated, live streptococci can be truncated, that truncations encoding the endopeptidase domain of the λSa2 endolysin are capable of exolysis, i.e., lysis from without lytic activity, and that truncations of the λSa2 endolysin can be used as an antimicrobial treatment for Streptococcal-induced diseases as well as Staphylococcal-induced infection and diseases, including infection and disease caused by multidrug-resistant strains.

In accordance with this discovery, it is an object of the invention to provide nucleic acid molecules encoding the truncated λSa2 endolysin polypeptides.

It is also an object of the invention to provide an antimicrobial truncated λSa2 endolysin which is functional in that it retains its properties for exolysis of the peptidoglycan cell wall of streptococcal bacteria and in fact demonstrates enhanced exolysis activity as compared to the native, non-truncated λSa2 endolysin.

It is a further object of the invention to provide a nucleic acid encoding an antimicrobial fusion protein formed from a nucleic acid encoding a functional λSa2 truncated endolysin, i.e., the endopeptidase domain, in combination with nucleic acid encoding one or both of the Cpl-7 cell wall-binding domain(s) of the native λSa2 endolysin thereby enhancing the exolysis of *streptococcus* and also extending the targets that can be lysed from without to *staphylococcus*.

It is a further object of the invention to provide a nucleic acid encoding an antimicrobial fusion protein formed from a nucleic acid encoding a functional λSa2 truncated endolysin, i.e., the endopeptidase domain, in combination with nucleic acid encoding a SH3b cell wall-binding domain thereby enhancing the exolysis of *staphylococcus* over and above that seen with the fusion nucleic acid encoding a functional λSa2 truncated endolysin comprising the endopeptidase domain in combination with the Cpl-7 cell wall-binding domains.

An added object of the invention is to provide a nucleic acid sequence encoding truncated λSa2 endolysin polypeptides according to the invention as an encoding sequence which allows disease resistance to be imparted to the organism. It is well understood that this sequence can also be used in combination with another sequence, or sequences, encoding one or more disease resistant properties.

An additional object of the invention is to provide a host organism into which the λSa2 truncated endolysin gene, according to the invention can be introduced so as to produce a truncated endolysin having enhanced endopeptidase activity.

An additional object of the invention is to provide a host organism into which the truncated λSa2 endolysin gene or fusion gene encoding additional cell-wall binding proteins according to the invention can be introduced so as to produce a fusion endolysin having enhanced endopeptidase activity.

An added object of the invention is to provide compositions useful for the treatment of disease caused by the bacteria for which the truncated λSa2 endolysin is specific and effective.

Also part of this invention is a kit, comprising a composition for treatment of disease caused by the bacteria for which the truncated λSa2 endolysin and fusions comprising truncated λSa2 endolysin are specific.

Other objects and advantages of this invention will become readily apparent from the ensuing description.

BRIEF DESCRIPTION OF THE DRAWINGS

FIG. 1A shows a schematic of the Lambda Sa2 endolysin and the six deletion constructs. FIG. 1B shows the purity in SDS PAGE analysis of the full length and deletion construct proteins from nickel column chromatography. Lane M, markers; Lane 1, λSa2-ECC; Lane 2, λSa2-G; Lane 3, λSa2-CG; Lane 4, λSa2-CCG; Lane 5, λSa2-EC; Lane 6, λSa2-E; Lane 7, λSa2.

FIG. 3A shows the effect of calcium chloride concentration on specific activity of λSa2 full length endolysin. FIG. 3B shows the effect of pH on specific activity of λSa2 (black bars), λSa2-EC (white bars) and λSa2-ECC (striped bars). FIG. 3C shows the effect of sodium chloride on specific activity of λSa2 (diamonds), λSa2-EC (squares) and λSa2-ECC (triangles). Error bars=Std. Dev.

DETAILED DESCRIPTION OF THE INVENTION

Figure 1:
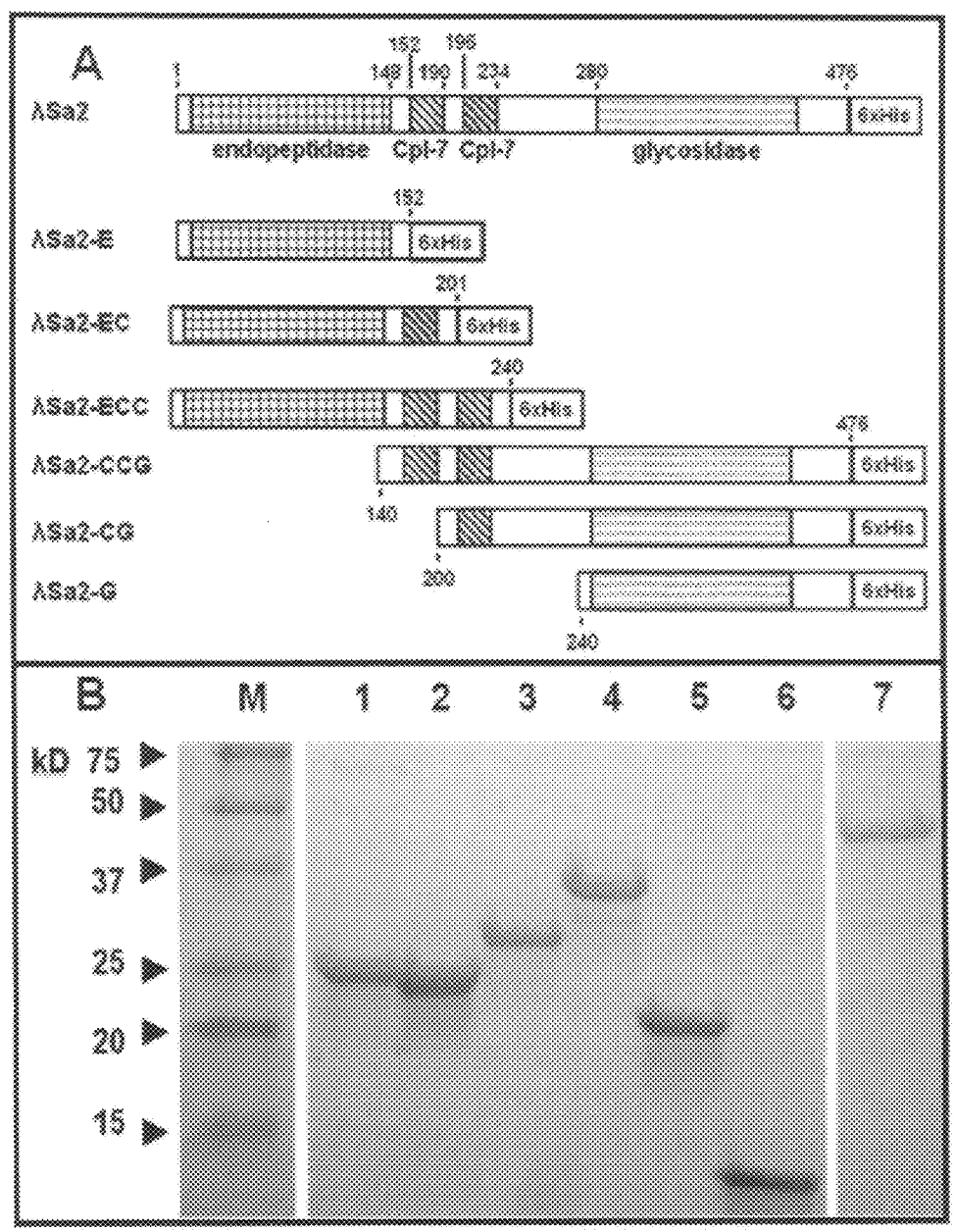
FIGS. 1A and 1B depict the structure of Lambda Sa2 prophage endolysin, deletion constructs, purification, and analysis.

The characterization of novel antimicrobials is becoming increasingly essential to combat the wave of newly emerging "superbugs" that are resistant to multiple antibiotics. Bacteriophage endolysins are gaining interest in this antimicrobial arena due to their ability to kill Gram positive pathogens at very low concentrations, and reports that they are refractory to resistance development (reviewed in Fischetti, supra). Toward this end, we have characterized the newly identified λSa2 prophage endolysin (Pritchard et al. 2007, supra) for its relative antimicrobial activity on numerous streptococci and have defined the protein domains that are essential for this bactericidal activity.

In this study we have used two different lytic assays to quantify the activity of the lysin and various truncated constructs. The turbidity reduction assay requires a robust enzyme in order to lyse large numbers of cells (starting concentration is >$10^9$ cells/ml), while the plate lysis assay can define relative activity with much lower amounts of bacteria, approximately $10^6$ cells. It is known that the assays to measure peptidoglycan hydrolase activities do not always agree quantitatively but do usually agree qualitatively (Kusuma and Kokai-Kun, supra).

The intact λSa2 lysin is a potent antimicrobial, i.e., as little as 0.1 µg results in a cleared spot on the plate lysis assay for multiple streptococcal pathogens. Although it has been reported that the intact lysin has the ability to digest prepared staphylococcal peptidoglycan (Pritchard et al. 2007, supra), it has little effect on most live staphylococcal species examined, when analyzed in both the turbidity reduction assay and the plate lysis assay. However, unexpectedly, there was significant activity from the truncated λSa2-ECC construct, i.e., as little as 1 µg was able to clear the lawn of multiple S. aureus including the MRSA strain USA300 and showed weak activity against S. xylosus. In order to optimize the activity of the full length lysin, we tested pH, salt, and calcium effects in the turbidity reduction assay against S. agalactiae, the species where the gene was first identified. The intact lysin is active in the turbidity reduction assay across a wide range of pH (5.5-9.5). Sodium chloride does not reduce the activity of the lysin until concentrations above 250 mM, with only a 50% reduction at the highest concentrations examined (430 mM NaCl). Calcium was not required for maximal activity, and the presence of 12 mM calcium reduced the activity of the lysin less than 30%. Salt and pH had a similar effect on two of the endopeptidase constructs (λSa2-EC, λSa2-ECC) as on the intact lysin, depressing the activity over 250 mM NaCl. In order to examine the endolysin and truncations for their antimicrobial efficacy under physiologically relevant conditions (as well as optimal conditions), turbidity reduction assays were performed at physiological pH (7.5) and salt concentration (150 mM), which yields near maximal activity for all constructs examined.

To identify the domains required for full activity, we dissected the lysin gene via deletion analysis. The goal was to produce truncated proteins harboring various combinations of domains to determine 1) the contribution of each domain to the lysis of live cells and 2) the particular domain which was active on each bacterial species tested. Turbidity reduction assays and plate lysis assays indicate that it is the endopeptidase domain that harbors virtually all of the lytic activity for the streptococcal pathogens examined. Only weak lysis was observed for the glycosidase domain and of the many streptococcal pathogens, only four were lysed with this domain (*S. equi* subs. *equi*, *S. dysgalactiae* subs. *equisimilis*, *S. pyogenes*, *S. uberis*). In the plate lysis assay, the glycosidase domain never achieved 10% of the endopeptidase domain activity. Despite the report that the glycosidase domain could cleave staphylococcal peptidoglycan (Pritchard et al. 2007, supra), no detectable lysis was observed for staphylococcal pathogens by any of the glycosidase domain constructs.

The endopeptidase domain without a Cpl-7 domain (λSa2-E) showed weak lytic activity in plate lysis assays. The addition of one Cpl-7 domain increased this activity, but addition of the second Cpl-7 domain achieved wild type activity levels or greater. Two streptococcal strains (*S. agalactiae*, *S. uberis*) showed a heightened susceptibility to the dual Cpl-domain endopeptidase construct (λSa2-ECC), achieving higher rates of lysis in the turbidity reduction assay than the full length (native) endolysin protein. However, the plate lysis assay did not verify this result at the lowest concentrations tested, suggesting that the intact lysin is the strongest lytic form against its host genus, streptococci. However, there was more lytic activity in λSa2-ECC against staphylococci than the full length λSa2 parental protein in the plate lysis assay. The parental protein showed weak lysis against all of the *Staphylococcus aureus* tested, while the two Cpl-7 domain endopeptidase construct was able to lyse all three of the *S. aureus* strains and *Staphylococcus hyicus* and *Staphylococcus xylosus*. Thus, both lytic domains require Cpl-7 cell wall-binding domains in order to achieve their respective maximal activities in the truncated constructs.

The need for cell wall-binding domains is not unprecedented with many lysins showing an absolute need for their cell wall-binding domains in order to achieve maximal activity. However, it is somewhat unusual to have the cell wall-binding domains located at the mid region of the endolysin, as most cell wall-binding domains are located at the C-terminus of phage lysins (Hermoso et al., supra; Loessner, supra). It was also unexpected that the λSa2 prophage endolysin shows less lytic activity toward live *S. agalactiae* than many other streptococcal species even though the λSa2 prophage endolysin was isolated from the *S. agalactiae* genome (Pritchard et al. 2007, supra). However, this is not unprecedented, for the B30 endolysin was shown to have higher activity toward *S. dysgalactiae* than its host *S. agalactiae* (Donovan, unpublished data). The fact that *S. aureus* and *S. agalactiae* share the same sequence at the site of λSa2 endopeptidase cleavage in the stem peptide of their peptidoglycan, but yet are lysed at very different efficiencies, led us to examine the role of other cell wall structures that might facilitate the level of activity that we observed.

Very little is known about the actual binding of most endolysins to peptidoglycan, although several endolysins and several binding domains of endolysins have been crystallized (Hermoso et al., supra). One of the most well characterized cell wall-binding domains is the SH3b of ALE-1, which has been crystallized and is known to direct binding of the endopeptidase domain to the *S. aureus* peptidoglycan substrate, the pentaglycine interpeptide bridge (Lu et al. 2006a. *J. Biol. Chem.* 281:549-558). In a separate set of experiments, Schneewind and colleagues have also shown that lysostaphin (99% identical to ALE-1) also binds to the pentaglycine bridge (Grundling and Schneewind, supra). How cell wall structures other than peptidoglycan might alter the endolysins binding domains' ability to find the target substrate has not yet been determined. However, what is known is that the basic peptidoglycan structure does not usually change with changing growth conditions (Schleifer and Kandler, supra); whereas, other cell wall structures are altered by environment and growth conditions, e.g., biofilms are one of the most extreme examples where growth conditions can alter cell wall structure (Davies, D. 2003. *Nat. Rev. Drug Discov.* 2:114-122; Resch et al. 2005. *Appl. Environ. Microbiol.* 71:2663-2676). Similarly, the susceptibility of some staphylococcal strains to lysostaphin is known to reflect differences in cell wall structures, namely teichoic acid content (Koehl et al., supra). This 'other cell wall structure' effect on endolysin activity is likely analogous to the ability of λSa2 endolysin to readily digest staphylococcal peptidoglycan preparations (Pritchard et al. 2007, supra), but the same lysin yields very poor lysis of growing staphylococcal cells.

The Cpl-7 cell wall-binding domain was first discovered in the cpl7 lysozyme encoded by the *S. pneumonia* bacteriophage Cp-7. In the cpl7 protein, there are three tandem C-terminal Cpl-7 domains. This domain has never been shown directly to bind to cell walls, but due to its C-terminal position, and comparison with other related lysins, it was determined to be a cell wall-binding domain (Garcia et al., supra). Although numerous pneumococcal phage endolysins are known to require choline binding for activity, the Cpl-7 domain is not believed to be a choline-binding domain. A search of the Interpro domain databases identifies 21 related sequences (Retrieved from the Internet: <URL: bi.ac.uk/interpro/ISpy?ipr=IPR013168). Of these 21 proteins, three are known to be of phage origin. Of the 12 Cpl-7 domain harboring proteins with a known function, two are phage lysins and the remaining 10 are characterized as lysozymes or transglycolases, functions known to be encoded by peptidoglycan hydrolases. The domain can apparently function at N-terminal, mid-protein or C-terminal positions in the protein, with examples of each in the dataset. Seven of the 21 proteins harboring these domains are of streptococcal origin, sharing a nearly identical structure as the λSa2, with an N-terminal amidase-5, a C-terminal glucosaminidase domain and either one or two midprotein Cpl-7 domains. The presence of either one or multiple Cpl-7 domains in these proteins is consistent with our λSa2 deletion analysis findings that either one or two Cpl-7 domains yield an active enzyme.

The highly active λSa2-ECC construct containing a single endopeptidase lytic domain and λSa2 cell wall-binding domains, i.e., two Cpl-7 domains, was modified by replacing the two Cpl-7 domains with the SH3b cell wall-binding domain from the bacteriocin lysostaphin. This modification increased the antimicrobial activity of this λSa2-ECC streptococcal phage endolysin protein fragment on staphylococcal cells approximately 10 fold. This is the first example where molecular engineering of a streptococcal bacteriophage peptidoglycan hydrolase enzyme resulted in a better antimicrobial for use against staphylococcal pathogens Another subject of the invention is the use of a nucleic acid sequence encoding a truncated λSa2 prophage endolysin according to the invention as an encoding sequence which allows disease resistance to be imparted to the organism. It is well understood that this sequence can also be used in combination with another sequence, or sequences, encoding or enhancing, one or more disease resistant properties. The present invention therefore also relates to a strategy of generating a nucleic acid sequence encoding a chimeric endolysin according to the invention, this process being defined herein.

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding a truncated λSa2 prophage endolysin related protein (truncation or fusion) as defined above. By host organism there is to be understood any single-celled or lower or higher non-human multi-celled organism into which λSa2 prophage endolysin gene according to the invention can be introduced. The regulatory elements required for expressing the nucleic acid sequence encoding a truncated λSa2 prophage endolysin are well known to those skilled in the art and depend on the host organism. The means and methods for identifying and choosing the regulatory elements are well known to those skilled in the art and widely described in the literature.

The present invention also relates to a cloning and/or expression vector for transforming a host organism containing at least the truncated λSa2 prophage endolysin gene as defined hereinabove. This vector comprises, in addition, to the above truncated λSa2 prophage endolysin gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the λSa2 prophage endolysin according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional λSa2 prophage endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of λSa2 prophage endolysin" refers to all fragments of λSa2prophage endolysin that retain λSa2 prophage endolysin activity and function to lyse staphylococcal bacteria.

Modifications of the λSa2 prophage endolysin primary amino acid sequence may result in further mutant or variant proteins having substantially equivalent activity to the λSa2 prophage endolysin polypeptides described herein. Such modifications may be deliberate, as by site-directed mutagenesis, or may occur by spontaneous changes in amino acid sequences where these changes produce modified polypeptides having substantially equivalent activity to the λSa2 prophage endolysin polypeptide. Any polypeptides produced by minor modifications of the λSa2 prophage endolysin primary amino acid sequence are included herein as long as the biological activity of λSa2 prophage endolysin is present; e.g., having a role in pathways leading to lysis of streptococcal or staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass, temperatures in the range of about 1° C. to about 20° C., depending upon the desired degree of stringency as otherwise qualified herein. Thus, isolated sequences that encode a λSa2 prophage endolysin polypeptide and which hybridize under stringent conditions to the λSa2 prophage endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have λSa2 prophage endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the λSa2 prophage endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, λSa2 prophage endolysin activity as described herein. Such variants may result from, for example, genetic polymorphism or from human manipulation. Biologically active variants of a native λSa2 prophage endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired λSa2 prophage endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of λSa2 prophage endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat. or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmids, Constructs and Strains

The strains used include: the bovine mastitis isolates *S. agalactiae, S. dysgalactiae, S. uberis, S. chronogenes, S. epidermis, S. simulans, S. warneri,* and *S. xylocus* (a gift from M. Paape, USDA, Beltsville, Md.). *S. dysgalactiae* subs. *equisimilis* 26RP66 (Rockefeller Univ. strain), *S. equi* subs. *equi* (ATCC 9528), *S. equi* subs. *zooepidemicus*

(ATCC 700400), and *S. aureus* RN4220 (originally from Richard Novak), were each a gift from Daniel Nelson, Univ. MD. Other staphylococcal strains include *Staphylococcus aureus* Newbolt 305 capsular polysaccharide serotype 5 (ATCC 29740), and the MRSA USA300, from NARSA. *S. pyogenes* (MGAS 802A374), GES and GGS were gifts from David Pritchard, Univ. Alabama Birmingham.

The LambdaSa2 gene in pET21a (EMD Biosciences, San Diego, Calif.) was obtained as a gift from David Pritchard (Pritchard et al. 2007, supra). Inducible plasmid constructs were created in pET21a for introduction of a C-terminal His-tag. Gene fragments were amplified with PCR primers (Table I) engineered with either an NdeI or XhoI site designed to introduce appropriate restriction enzyme sites for subcloning into pET21a. PCR products were gel purified, digested appropriately with restriction enzymes, purified over a Micro Bio Spin P30 desalting column (BioRAD, Inc.) and introduced into similarly digested, dephosphorylated and gel purified pET21a via conventional means. All constructs are C-terminally His-tagged with eight additional amino acid residues introduced at the C-terminus corresponding to the XhoI site (Leu-Glu) followed by six His residues. All subcloning was performed in *E. coli* DH5a (Invitrogen, Carlsbad, Calif.) for plasmid DNA isolation and sequence verification of all constructs. pET21a constructs were induced in *E. coli* BL21 (DE3) (EMD Biosciences, San Diego, Calif.).

TABLE 1

PCR Primers

| | | SEQ ID NO: |
|---|---|---|
| LSa2 X HO 145R | 5'-TCCTTGCTCGAGAGCTCCGCTTTTC-3'* | 1 |
| LSa2 X HO 201R | 5'AGCGATCTCGAGTTGAACAAG-3' | 2 |
| LSa2 X HO 240R | 5'-TTGAGCCTCGAGCGGCTCAGAG-3' | 3 |
| LSa2 X HO 468R | 5'-GTGGTGCTCGAGAACTGGC-3' | 4 |
| LSa2 X NDE AA1F | 5'-GATATACATATGGAAATCAACAC-3' | 5 |
| LSa2 X NDE 140F | 5'-TGCTACCATATGCGTTTGAAAAG-3' | 6 |
| LSa2 X NDE 200F | 5'-GTTGACCATATGGTTCAAGAGGTAATCGCT-3' | 7 |
| LSa2 X NDE 240F | 5'-CAGCCCCATATGCCGTTTAAGG-3' | 8 |

* Engineered restriction enzyme sites are underlined.

The LambdaSa2 (λSa2) endolysin contains an N-terminal amidase-5 domain and a C-terminal amidase-4 domain (FIG. 1). The endopeptidase activity (from the amidase-5 domain) cleaves between the D-Glutamine and L-Lysine of the peptidoglycan stem peptide. The amidase-4 activity is an N-acetylglucoseaminidase that cleaves the sugar backbone of peptidoglycan (Pritchard et al. 2007, supra). In the protein midregion, between the two lytic domains, there are two tandem Cpl-7 cell wall-binding domains [Retrieved from the Internet: <URL: pfam.janelia.org/family?acc=PF08230]; Garcia et al., supra; Lopez and Garcia. 2004. *FEMS Microbiol. Rev.* 28: 553-580). The work of Pritchard et al. (2007, supra) characterized the exact cleavage sites of the λSa2 endolysin through the use of prepared cell wall peptidoglycan. To determine the role of the lytic domains and Cpl-7 cell wall-binding regions in the lysis of live cells, we created a series of both C- and N-terminal deletion constructs (FIG. 1). The logic behind the design of these constructs is to isolate each lytic domain either by itself, with just one or with both Cpl-7 cell wall-binding domains. The purity of the nickel column purified, His-tagged proteins is illustrated in the SDS PAGE analysis (FIG. 1). There were no bands visualized in the gel outside of the region displayed.

The nucleic acid molecules encoding the constructs E, E-C, E-CC, and E-Sh3b comprise nucleotides encoding C-terminal LEHHHHHH (SEQ ID NO:17) residues and are identified by SEQ ID NOs: 9, 11, 13, and 15, respectively. The proteins encoded by these nucleic acid sequences are identified by SEQ ID NOs: 10, 12, 14, and 16, respectively. The expressed proteins are His-tagged with eight additional amino acid residues introduced at the C-terminus corresponding to the XhoI site (Leu-Glu) followed by six His residues.

Example 2

Protein Purification and Analysis

Mid log phase ($OD_{600nm}$ of 0.4-0.6) *E. coli* cultures harboring pET21a-derived expression vectors were grown under ampicillin selection, chilled on ice for 30 min, induced with 1 mM IPTG, and incubated with shaking for 18 h at 19° C. *E. coli* harvested from 100 ml cultures were suspended in 2 ml lysis buffer (50 mM $NaH_2PO_4$, 300 mM NaCl, 10 mM imidazole, pH 8), sonicated on ice for 15×5 sec pulses separated by 15 sec rests, and centrifuged at 6800 rpm for 30 min. in a Sorvall HS4 rotor. The cleared supernatant was applied to 1 ml Ni-NTA Agarose (nickel matrix) in a slurry and mixed gently for 1 hour at 4° C. (Qiagen). The wash and elution buffer profiles were empirically determined for all constructs to be 10 ml of 10 mM imidazole, 20 ml of 20 mM imidazole and eluted into 1.2 ml of 250 mM imidazole in the same phosphate buffered saline (50 mM $NaH_2PO_4$, 300 mM NaCl, pH 8.0). 1% glycerol was added immediately to the eluate to avoid potential solubility problems that are known to exist for His-tagged proteins (and which we have experienced previously) (Woestenenk et al. 2004. *J. Struct. Funct. Genomics* 5:217-229). All samples were then either converted to storage buffer (10 mM Tris-Cl pH 7.5, 150 mM NaCl with 1% glycerol) via a Zeba desalting column (Pierce) that was previously converted to storage buffer or assayed directly in nickel column elution buffer with 1% glycerol. All samples were 0.22 micron filter sterilized for use in plate lysis assays. Sterilized proteins were stored at 4° C. or -80° C. until used. Protein concentration determinations were via BCA Protein kit (Pierce). Purity of each preparation was determined via SDS-PAGE.

The purified constructs and Precision Plus protein standards (Bio-Rad) were analyzed with 15% SDS-PAGE in Tris-Glycine buffer at 150 volts for 1.5 hours in Criterion Precast gels (Bio-Rad, Inc., Hercules, Calif.), according to manufacturer's instructions. Gels were stained in Coomassie stain for one hour and then de-stained for 6-18 hours via conventional methods. The proteins purified on the nickel column retained the His tags, thus the His tags were present in the various assays. His tags can be removed by methods well known and practiced in the art.

Example 3

Turbidity Reduction Assay

The turbidity assay measures the drop in optical density (OD) resulting from lysis of the target bacteria with the phage endolysin-derived protein. A standardized turbidity assay modified from (Donovan et al. 2006a. *Appl. Environ. Microbiol.* 72:2988-2996) with *S. aureus* grown to logarithmic phase ($A_{600nm}$=0.4-0.6) at 37° C. in Brain Heart Infusion broth (DIFCO, Franklin Lakes, N.J.) were performed in a 96 well dish and analyzed in a plate reader. Log phase cultures were harvested at 4° C. by centrifugation and stored on ice less than 4 hours until just before the assay when they were suspended in 150 mM NaCl, 10 mM Tris-Cl, pH 7.5 or 50 mM Phosphate buffer, pH 7.5 to an $A_{600nm}$ ~1.0. Enzyme samples are added to three wells of a 96 well dish in 100 μl of buffer (Ni-NTA elution buffer or storage buffer were shown to be equivalent). All samples are performed in triplicate. The assay is started by the addition of 100 μl of cells in buffer at $A_{600m}$ ~1.0 via multi channel pipettor. A 'no enzyme control' of buffer and cells is included. $A_{600nm}$ readings are taken every 20 seconds for 5 minutes. The readings for each well are transferred electronically to an Excel spreadsheet where they are analyzed in a sliding window over each group of 3 consecutive time points during the five minute period, to identify the highest instantaneous change in $A_{600nm}$ for each well. The absolute values of $\Delta A_{600nm}$ for each group of 3 time points are ranked and the optimum chosen based on highest absolute value and reproducibility in the triplicate wells. A similarly calculated buffer plus cells alone control value from triplicate wells is then subtracted from the highest ranked value for each experimental well, and the values for the triplicate wells averaged to give a $\Delta OD_{600nm}$/minute. This value is then divided by the ug of enzyme protein in the sample tested to give a specific activity $\Delta OD_{600nm}$/ug/min. The turbidity reduction assays are repeated with multiple independent protein isolations to verify the results, but only representative assays are presented, due to the high day-to-day variability in the results, presumably due to variations in the cell culture preparations.

Figure 2:
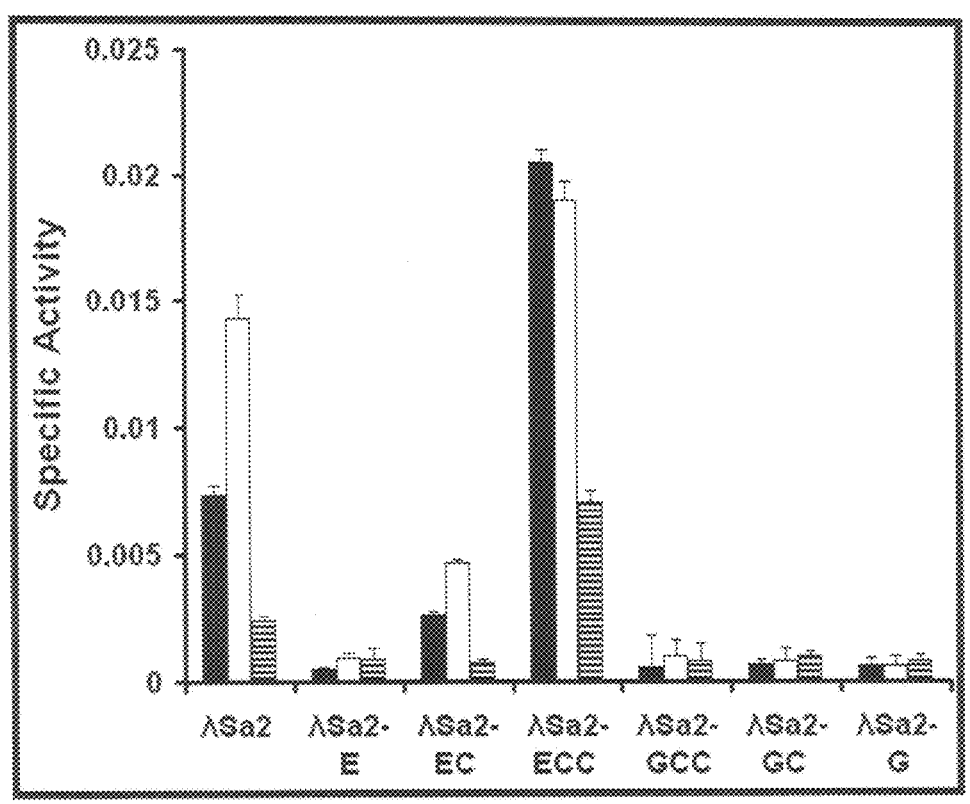
FIG. 2 depicts activity of Lambda Sa2 endolysin and deletion constructs on three streptococcal species in turbidity reduction assays. S. agalactiae (black), S. dysgalactiae (white), S. uberis (stripes). Error bars=Std. Dev.

Purified proteins from all seven constructs depicted in FIG. 1 were tested in turbidity reduction assays for their ability to lyse log phase cells from three streptococcal mastitis causing pathogens: *S. agalactiae*, the species where the λSa2 prophage genome was discovered, *S. dysgalactiae* and *S. uberis*. The results indicate that the full-length protein (λSa2), and each of the endopeptidase domain-harboring constructs that also have at least one Cpl-7 domain (λSa2-EC, λSa2-ECC) were active against all three species (FIG. 2). The λSa2-ECC construct has a similar (or higher activity) than the full length protein against all three strains. The glycosidase domain constructs (λSa2-CCG, λSa2-CG, λSa2-G) and the endopeptidase construct with out any cell wall-binding domain (λSa2-E) showed very little activity in the turbidity reduction assay.

Figure 3:
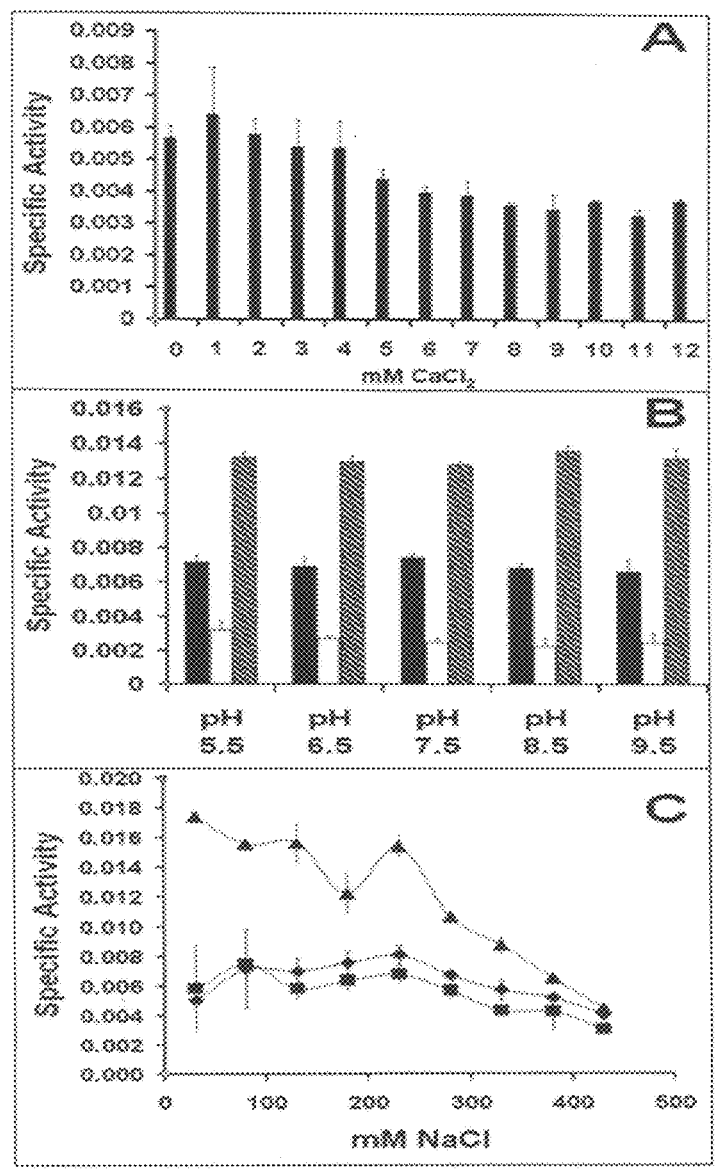
FIGS. 3A-3C show optimization of the turbidity reduction assay for LambdaSa2 endolysin and deletion constructs. All assays were performed on log phase S. agalactiae.

Prior to further characterization of the activities, the turbidity reaction conditions were optimized with the full length construct and the two active deletion constructs (FIG. 3). To address previous findings that the *S. agalactiae* bacteriophage B30 endolysin required 10 mM calcium for optimal activity (Pritchard et al. 2004, supra), the full length λSa2 protein was examined for the effect of calcium. There was no enhancement of activity with the addition of between 1 and 12 mM $CaCl_2$. There was a trend toward a reduced activity with the addition of calcium, but the addition of 12 mM $CaCl_2$ yielded less than a 30% reduction in activity (FIG. 3A). Similarly, the three high-activity constructs (λSa2, λSa2-EC, λSa2-ECC) were shown to maintain their activity across a broad range (pH 5.5 to 9.5) of physiologically relevant pH (FIG. 3B). Interestingly, when testing the effect of NaCl concentration on the constructs, there was a reduction in activity above 250 mM NaCl on all three high activity constructs (λSa2, λSa2-EC, λSa2-ECC). This was most dramatic with the λSa2-ECC protein, with 400 mM reducing the activity to the parental endolysin λSa2 activity level (FIG. 3C). Due to the predicted use of this protein as an antimicrobial, it was decided to perform subsequent turbidity reduction assays at near physiological conditions (pH 7.5 and 150 mM NaCl) where all active constructs appear to have near maximal activity.

Figure 4:
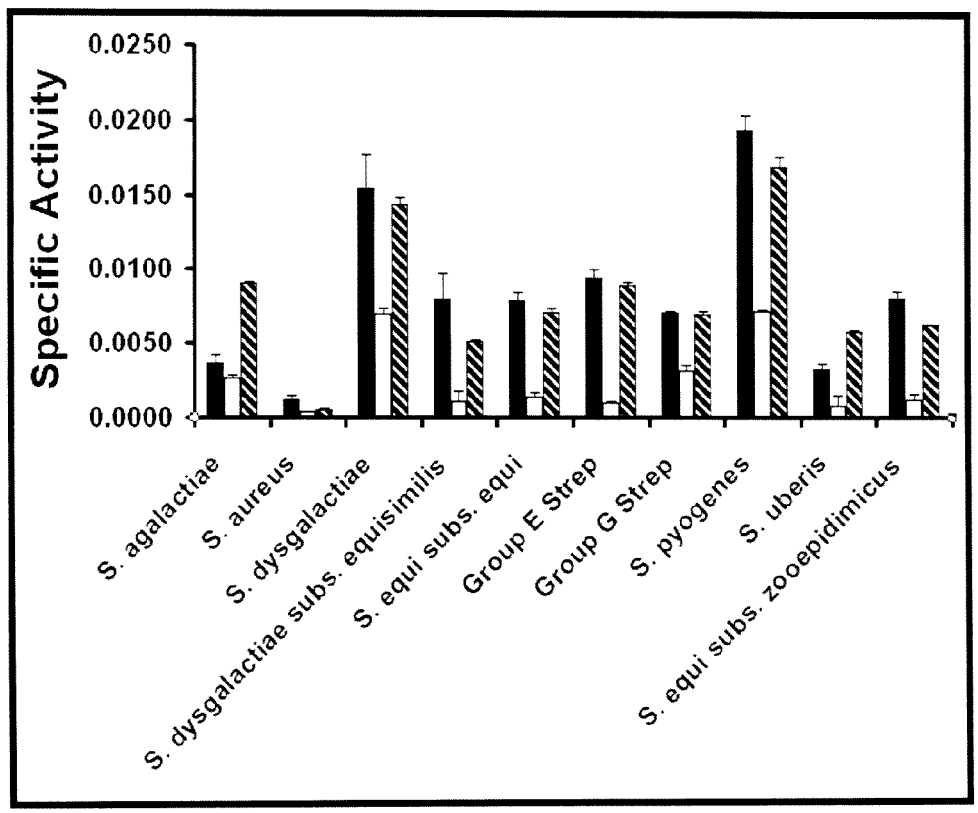
FIG. 4 depicts the turbidity reduction activity of LambdaSa2 endolysin and two deletion constructs on multiple species. λSa2 (black), λSa2-EC (white) λSa2-ECC (striped). Error Bars=Std. Dev.

The lytic profile of the three most active constructs was tested in turbidity reduction assays against multiple streptococcal and staphylococcal pathogens (FIG. 4). Pathogens from these two genera were chosen for two reasons. First, it was reported previously that the endolysin could digest both *S. pneumoniae* and *Staphylococcus aureus* cell wall peptidoglycan (Pritchard et al. 2007, supra) and lyse both species on plate lysis assays (personal communication, David Pritchard). Second, it is known that both staphylococci and streptococci harbor the same peptidoglycan amino acid sequence in the region of the stem peptide (L-Ala-D-Gln-L-Lys-D-Ala) where the λSa2 endopeptidase cleaves (between D-glutamine and L-Lysine). Similarly, the λSa2 glucosaminidase domain cleaves the sugar backbone structure common to all peptidoglycan (Schleifer and Kandler, supra; Pritchard et al. 2007, supra).

The three most active constructs (λSa2-CCG, λSa2-CG, λSa2-G) were shown in turbidity reduction assays to be active against mid-log phase *S. agalactiae*, *S. dysgalactiae*, *S. dysgalactiae* subs. *equisimilis*, *S. equi* subs. *equi*, *S. equi* subs. *zooepidimicus*, GES, GGS, *S. pyogenes*, *S. uberis*, with *S. pyogenes* and *S. dysgalactiae* showing the highest susceptibility (FIG. 4). Interestingly, while the λSa2-ECC construct showed the highest activity against both *S. agalactiae* and *S. uberis* in this and prior turbidity reduction assays, most of the strains tested showed a nearly identical level of susceptibility to both the full length endolysin λSa2 and the endopeptidase with two Cpl-7 domains (λSa2-ECC). In these 5 minute turbidity reduction assays, none of the truncated or full length protein constructs showed significant activity against *S. aureus* (FIG. 4) or any of the staphylococcal strains tested (*S. chromogens*, *S. hyicus*, *S. simulans*, *S. warneri*, *S. xylosus*; data not shown).

Example 4

Plate Lysis Assay

Purified proteins for each construct were diluted in sterile nickel column elution buffer and six microliters containing (10, 1.0 and 0.1 μg) was spotted onto a freshly spread lawn of growing cells that had air dried for 30 min on tryptic soy agar plates. The spotted plates were air dried for 10 min in a laminar flow hood, and incubated overnight in a 37° C. environment. Scoring of the cleared spots occurred within 20 hr of plating the cells.

Figure 5:
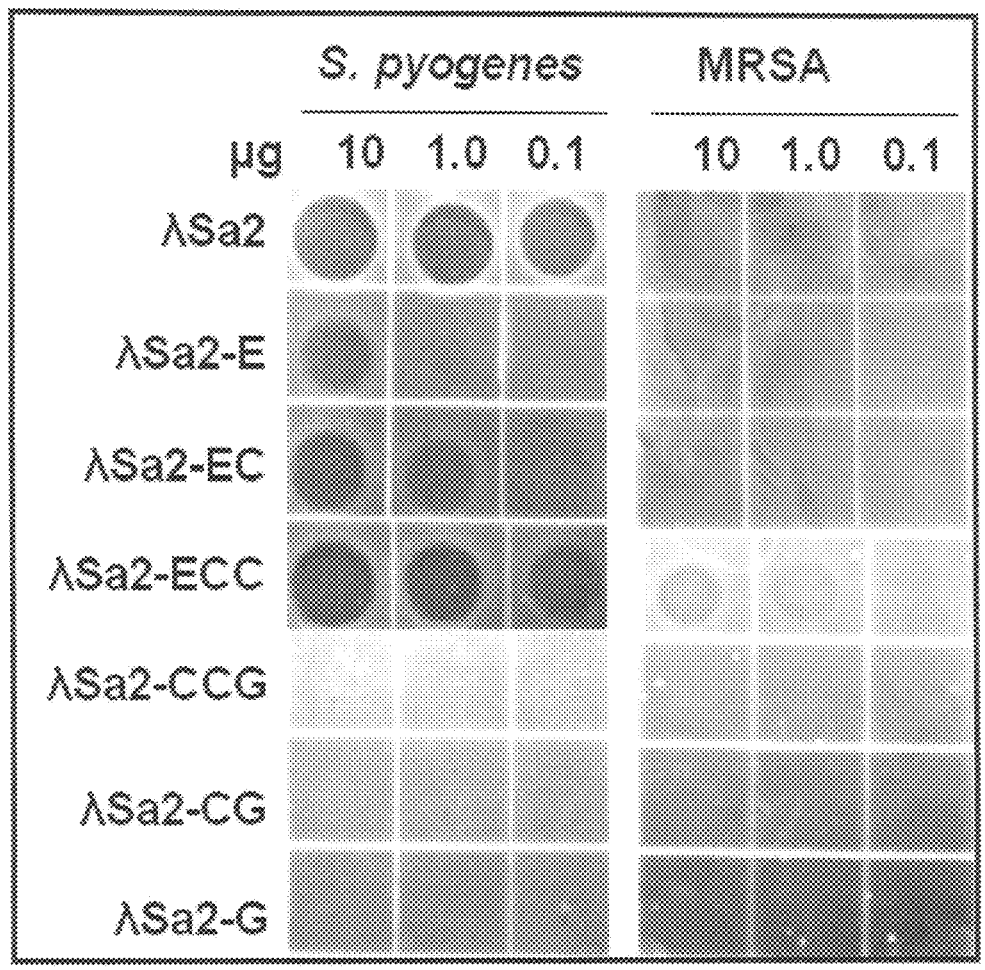
FIG. 5 shows plate lysis assay results with LambdaSa2 endolysin and deletion constructs on S. pyogenes and MRSA (USA300). 10, 1.0, and 0.1 µg of each construct was spotted in 6 µl of nickel column elution buffer. Some of the weaker activities (primarily the glycosidase domain constructs) were barely visible to the naked eye, and were not able to be captured in the photograph. Data for multiple strains is summarized in Table 2.

It has been shown that the standard methods to quantify peptidoglycan hydrolase activity (e.g. lysostaphin) do not always agree quantitatively (Kusuma and Kokai-Kun. 2005. *Antimicrob. Agents Chemother.* 49: 3256-3263). The turbidity reduction assay is a short assay, with a very high concentration of cells ($OD_{600nm}$ of $1.0 \geq 10^9$ cells/ml), such that a robust activity is required to yield a significant reduction in turbidity. To further characterize the activity levels, plate lysis assays were performed with the λSa2 constructs (FIG. 5). Plate lysis assays use a low level inoculum (compared to the turbidity reduction assay) and allow an overnight incubation. Thus, a low level enzymatic activity might reveal itself in the plate lysis assay which was not identified in the turbidity reduction assay. All constructs were spotted at three concentrations (10, 1 or 0.1 μg/6 μl spot) onto a Tryptic Soy Agar plate that was previously spread with an inoculum of a live culture of either streptococcal or staphylococcal cells. A representative plate with S. pyogenes is presented in FIG. 5. A cleared spot in the lawn indicates lysis of the pathogen. The complete data set is described in Table 2. The results in Table 2 are presented as −, +/−, +, ++ or +++.

The results in the plate lysis assay largely reflect the results of the turbidity assays, with the full length endolysin (λSa2) and dual Cpl-7 endopeptidase construct (λSa2-ECC) showing the highest activity on all streptococcal species tested (Table 2). However, with the added sensitivity of the plate lysis assay, the endopeptidase domain alone with no Cpl-7 domain (λSa2-E) showed some activity against most of the strains with only S. agalactiae, S. equi subs. equi and Group E Streptococcus showing no lysis by the endopeptidase domain alone. Unlike the turbidity assay, there was also some detectable activity from the glycosidase harboring constructs (λSa2-CCG, λSa2-CG) against several streptococcal cultures. S. dysgalactiae subs. equisimilis, S. equi subs. equi, S. pyogenes and S. uberis all showed clearing on the plate lysis assay with the truncated proteins harboring the glycosidase domain. Consistent with the endopeptidase domain's requirement of dual Cpl-7 domains for high activity, the glycosidase domain also showed higher activity with both cell wall-binding domains. S. uberis showed the greatest susceptibility to the glycosidase domain because the glycosidase domain alone, without a Cpl-7 domain, showed a cleared spot.

TABLE 2

Plate lysis assay results with multiple strains.

|  | λSa2 | λSa2-E | λSa2-EC | λSa2-ECC | λSa2-CCG | λSa2-CG | λSa2-CG |
|---|---|---|---|---|---|---|---|
| *Streptococcus* | | | | | | | |
| S. agalactiae | + | — | +/− | ++ | — | — | — |
| S. dysgalactiae | +++ | + | ++ | +++ | — | — | — |
| S. dysgalactiae subs. equisimilis | +++ | + | ++ | +++ | +/− | — | — |
| S. equi subs. equi | ++ | — | — | ++ | ++ | + | — |
| S. equi subs. zooepidimicus | ++ | +/− | + | +++ | — | — | — |
| Group E Strep | + | — | + | ++ | — | — | — |
| Group G Strep | +++ | + | ++ | +++ | — | — | — |
| S. pyogenes | +++ | + | ++ | +++ | +/− | +/− | — |
| S. uberis | ++ | +/− | ++ | ++ | ++ | ++ | + |
| *Staphylococcus* | | | | | | | |
| S. aureus (302) | +/− | — | — | + | — | — | — |
| S. aureus (USA300) | +/− | — | — | ++ | — | — | — |
| S. aureus (RN4220) | +/− | — | — | ++ | — | — | — |
| S. chromogenes | — | — | — | — | — | — | — |
| S. hyicus | — | — | — | + | — | — | — |
| S. simulans | — | — | — | — | — | — | — |
| S. warneri | — | — | — | — | — | — | — |
| S. xylosus | — | — | — | + | — | — | — |

+++ All three aliquots (10, 1.0, and 0.1 μg) of the construct produced a clear spot.
++ Two highest amounts yielded a clear spot.
+ Only the 10 μg aliquot yielded a clear spot.
+/− The 10 μg aliquot only yielded a weak or partially cleared spot.

The full-length λSa2 protein and the λSa2-ECC constructs were the only ones to show detectable activity against the staphylococcal species in the plate lysis assay (Table 2). The S. aureus strains all showed lysis by 10 μg of the full-length construct, while the MRSA strain USA300 was susceptible with as little as 1 μg (Table 2). The λSa2-ECC construct was the only construct that showed lytic activity toward S. hyicus and S. xyloses, and only with the 10 μg aliquot.

Example 5

λSa2-E-Lysostaphin SH3b" Fusion Construct and Activity

Sequences encoding the entire mature lysostaphin (246 amino acid residues) were PCR-amplified from pET21a-lysostaphin vector using engineered primers harboring an NdeI site in the forward primer and an XhoI site in the Reverse primer, and a lysostaphin vector template. The amplified fragment was subsequently digested with NdeI and XhoI restriction enzymes using standard procedures. The digested fragment was then ligated into an NdeI-XhoI digested pET21a vector (Novagen). The final construct expresses a version of mature lysostaphin with a single methionine residue introduced at the N-terminus, and an additional eight amino acid codons were introduced at the C-terminus (L E H H H H H H; SEQ ID NO:17) of the open reading frame, resulting from the vector encoded XhoI site and the six-His tag element inherent to the pET21a vector.

Figure 6:
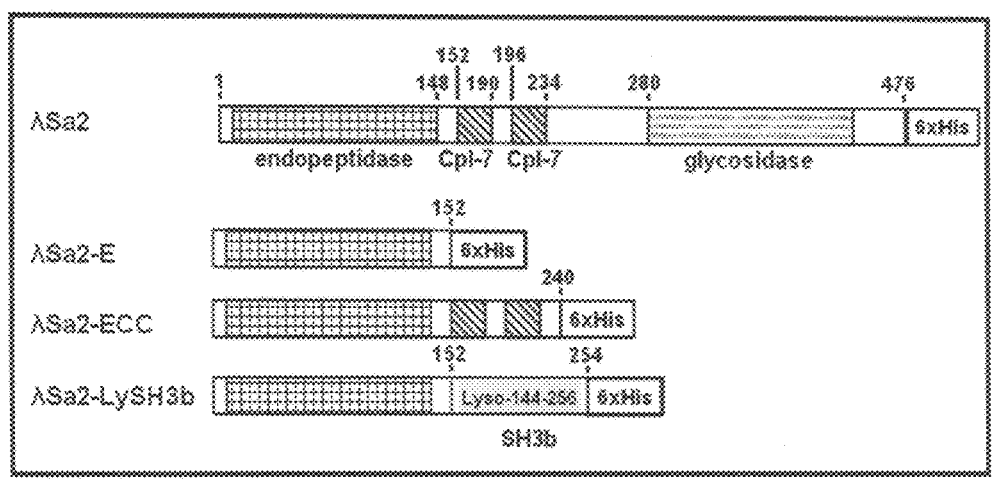
FIG. 6 shows both a schematic of the Lambda Sa2 prophage endolysin and the pertinent deletion and fusion constructs.

The final sequence of the pET21a-lysostaphin vector is 6108 bp (SEQ ID NO: 18). There is a StyI site located approximately 100 bp 3' to the translation stop signal of the six-His tag, in the pET21a vector sequences. We have taken advantage of this site in creating the "λSa2-E-lysostaphin SH3b" fusion. The pET21a-lysostaphin vector was first used as template to generate a PCR generated DNA fragment harboring the C-terminal amino acid residues 144-256 (including the SH3b cell wall binding domain) of this bacteriocin. The region was amplified with the primers LYSO SalI 144 F: 5'-GGAAAAGCAGTCGACACAGTAACT CC-3' (SEQ ID NO: 19) and pET21a STY I R: 5'-TAGAGGC-CCCAAGGGGTTATG-3' (SEQ ID NO:20). The LYSO SalI144 F introduces a SalI site at codon 144 (of the mature lysostaphin open reading frame) that is then introduced into the PCR amplified fragment. The amplified fragment was subsequently digested with Sal I and XhoI restriction enzymes using standard procedures. The digested fragment was then ligated into an XhoI-digested λSa2-E vector harboring just the endopeptidase domain in pET21a. SalI and XhoI create identical restriction enzyme site overhangs such that their digestion products can be ligated via standard procedures. The resultant construct encodes the first 152 amino acids of λSa2, i.e., the λSa2 endolysin, and the C-terminal 112 amino acids of the mature lysostaphin plus the C-terminal L E H H H H H H (SEQ ID NO:17) residues derived from the XhoI site and the 6×His-tag of the pET21a vector. The final construct was sequence-verified in the region of the protein coding sequences (FIG. 6).

Figure 7:
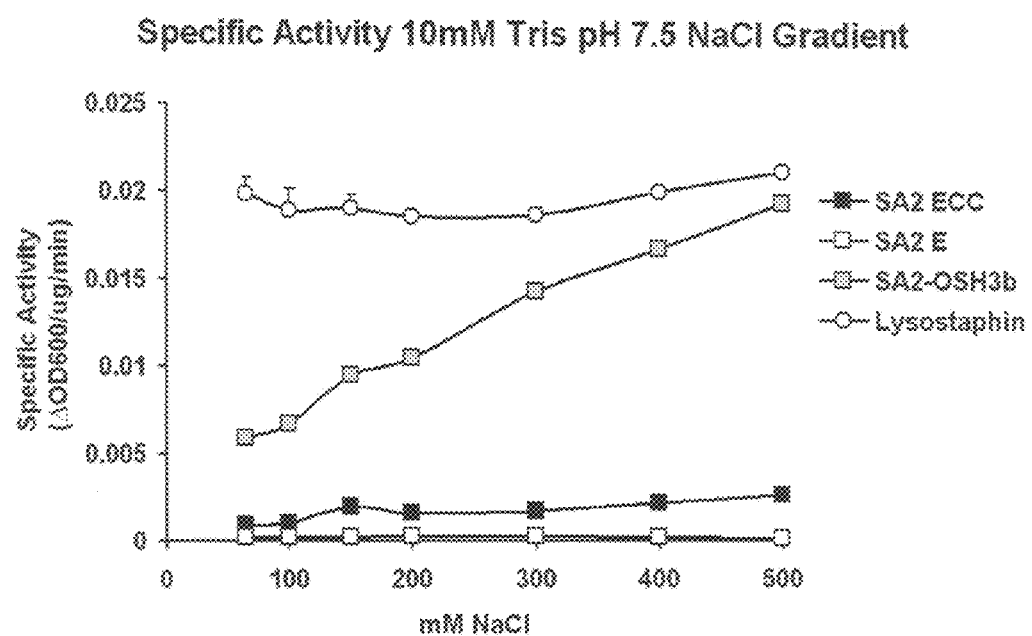
FIG. 7 depicts that the λSa2-E-lysostaphin SH3b fusion shows a 5-10 fold higher antimicrobial activity than either the λSa2-E or λSa2-ECC constructs in turbidity reduction assays with S. aureus at increasing NaCl concentrations. In turbidity reduction assays, the activity of the fusion constructs tested on live S. aureus cells prepared from mid-log phase liquid cultures approaches the same activity level as the bacteriocin lysostaphin at 500 mM NaCl.
Figure 8:
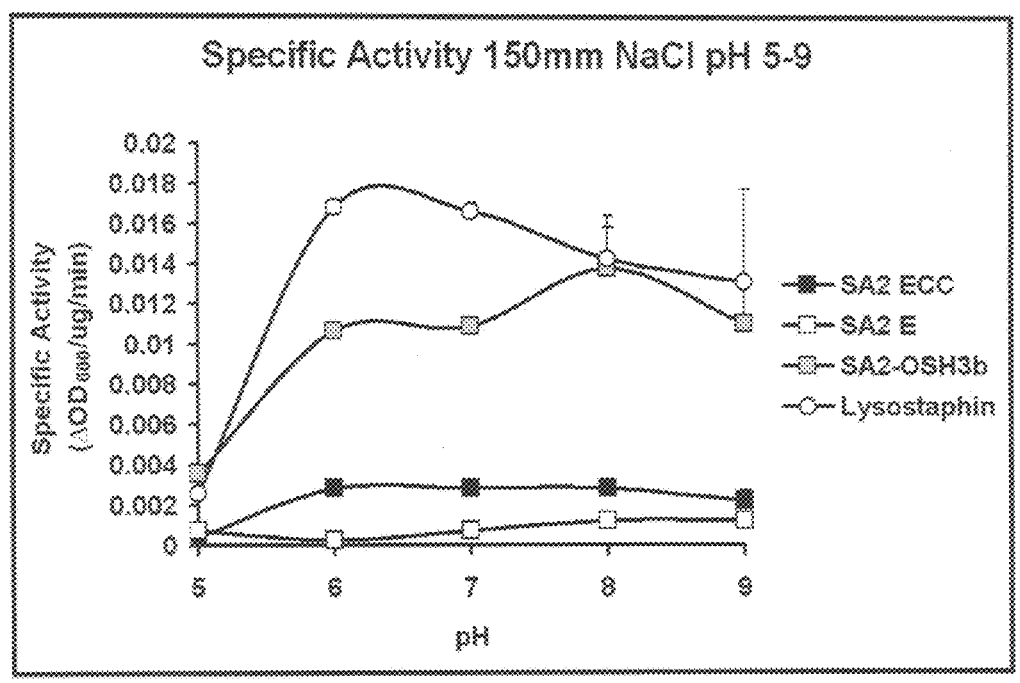
FIG. 8 shows that the λSa2-E-lysostaphin SH3b fusion achieves full activity in the pH range of 6 through 9. The activity level of the fusion is roughly 50% that of lysostaphin in physiological saline at pH 6 and 7, but nearly identical to lysostaphin activity at pH 8 and 9. Assay performed with turbidity reduction assays on live S. aureus cell preparations from mid-log phase liquid cultures.
Figure 9:
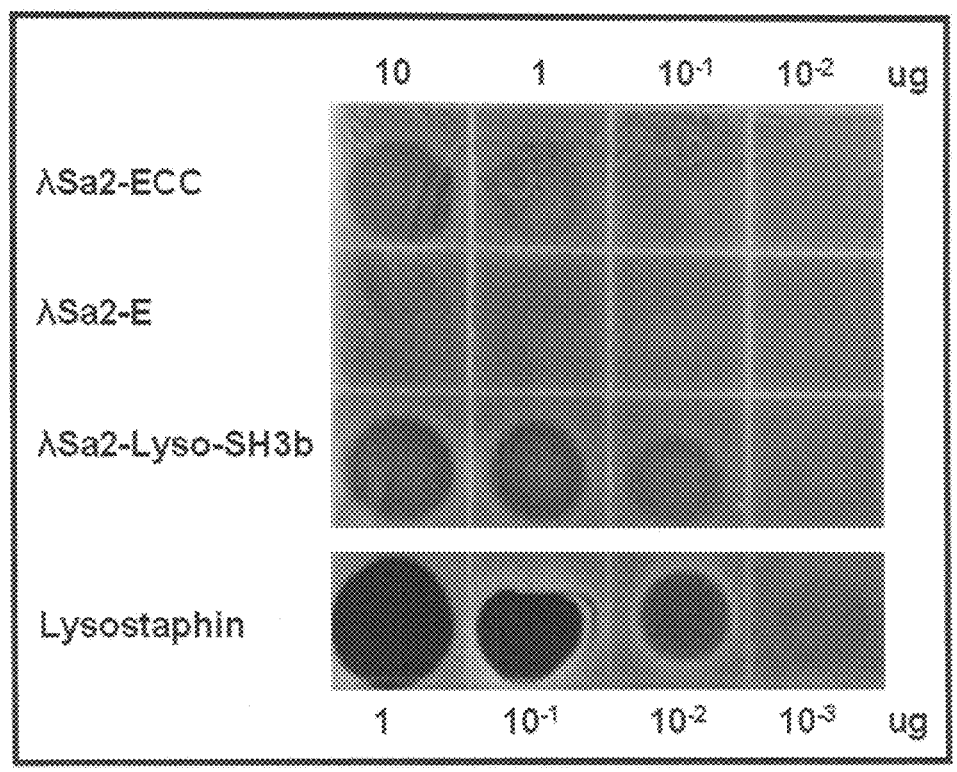
FIG. 9 shows that the λSa2-E-lysostaphin SH3b fusion construct has at least 10 fold more activity than either the λSa2-E or λSa2-ECC constructs in plate lysis assays with cells grown on agar plates.

When tested in turbidity reduction assays (FIGS. 7, 8) or plate lysis assays (FIG. 9), the λSa2-E-lysostaphin-SH3b fusion shows 5-10× heightened lytic activity at a wide range of pH and salt concentrations against staphylococci compared to the λSa2-ECC construct which harbors the same endopeptidase domain but with the native λSa2 Cpl-7 cell wall-binding domains (CC).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

I claim:

1. An isolated or recombinant cDNA sequence encoding an antimicrobial fusion endolysin enzyme molecule λSa2-ECC, wherein said λSa2-ECC is a truncation of the complete native λSa2 endolysin enzyme molecule, said λSa2-ECC consisting essentially of the native λSa2 endopeptidase domain; λSa2-E, two complete native λSa2Cpl-7 cell wall-binding domains (CC), and terminating with the amino acids leucine, glutamic acid, histidine, histidine, histidine, histidine, histidine, histidine, and said λSa2-ECC having the sequence SEQ ID NO:14.

2. The isolated or recombinant cDNA sequence of claim 1, wherein said cDNA has the sequence set forth in SEQ ID NO: 13.

3. The isolated or recombinant cDNA sequence encoding an antimicrobial fusion endolysin enzyme molecule, λSa2-E-lysostaphin SH3b fusion, said λSa2-E-lysostaphin SH3b consisting essentially of the native λSa2 endopeptidase domain, λSa2-E, and the SH3b cell wail-binding domain from the C-terminal region of the native lysostaphin molecule, and terminating with the amino acids leucine, glutamic acid, histidine, histidine, histidine, histidine, histidine, histidine, and said λSa2-E-lysostaphin SH3b fusion endolysin enzyme molecule having the sequence SEQ ID NO: 16.

4. The isolated or recombinant cDNA sequence of claim 3, wherein said cDNA has the sequence set forth in SEQ ID NO: 15.

5. A construct comprising the isolated or recombinant cDNA sequence of claim 1, wherein said cDNA is in operable linkage to a promoter that drives expression in a host cell.

6. A construct comprising the isolated or recombinant cDNA sequence of claim 3, wherein said nucleic acid is in operable linkage to a promoter that drives expression in a hot cell.

7. A cloning vector or an expression vector comprising the construct of claim 5.

8. A cloning vector or an expression vector comprising the construct of claim 6.

9. A process for transforming a host cell, comprising stably integrating the isolated or recombinant cDNA sequence of claim 1 or 3, or the construct of claim 5 or 6 into the host cell.

10. An isolated host cell transformed with the isolated or recombinant cDNA sequence of claim 1 or 3.

11. An isolated host cell transformed with the construct of claim 5 or 6, wherein said host cell is a single-celled or multi-celled organism into which the construct according to the invention can be introduced so as to produce an antimicrobial truncated endolysin.

12. A method of making a recombinant λSa2 truncated endolysin protein, said method comprising steps:
   a. introducing into a host cell the cDNA sequence of claim 1 or 3, or the construct of claim 5 or 6;
   b. culturing said cell under conditions suitable for expression of said protein; and
   c. recovering the protein so expressed.

* * * * *

SEQUENCE LISTING

<160> NUMBER OF SEQ ID NOS: 20

<210> SEQ ID NO 1
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 1
tccttgctcg agagctccgc ttttc                                          25

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
agcgatctcg agttgaacaa g                                              21

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 3
ttgagcctcg agcggctcag ag                                             22

<210> SEQ ID NO 4
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 4
gtggtgctcg agaactggc                                                 19

<210> SEQ ID NO 5
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 5
gatatacata tggaaatcaa cac                                           23

<210> SEQ ID NO 6
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 6
tgctaccata tgcgtttgaa aag                                           23

<210> SEQ ID NO 7
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 7
gttgaccata tggttcaaga ggtaatcgct                                    30

<210> SEQ ID NO 8
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 8
cagccccata tgccgtttaa gg                                            22

<210> SEQ ID NO 9
<211> LENGTH: 483
<212> TYPE: DNA
<213> ORGANISM: LambdaSa2 phage

<400> SEQUENCE: 9
atggaaatca acactgaaat agccattgcc tggatgtctg cacgtcaagg caaggtcagc    60
tattccatgg actaccgtga cggccctaac agctatgact gttccagctc tgtctattat   120
gctctcaggt cagctggtgc aagctcagca ggttgggcgg tcaacactga gtacatgcac   180
gattggctga ttaaaaacgg ttatgagctt attgctgaaa acgtggattg gaatgctgtc   240
cgtggtgata tagcaatttg gggcatgcga gggcactcaa gcggagctgg tggtcatgta   300
gtcatgttta ttgaccctga aaatatcatt cactgtaact gggcaaataa tggcatcaca   360
gtgaacaact acaatcagac agcggctgct agtggctgga tgtattgcta cgtttaccgt   420
ttgaaaagcg gagcttctac ccaaggaaaa agccttctcg agcaccacca ccaccaccac   480
tga                                                                483

<210> SEQ ID NO 10
<211> LENGTH: 160
<212> TYPE: PRT

<213> ORGANISM: LambdaSa2 phage

<400> SEQUENCE: 10

```
Met Glu Ile Asn Thr Glu Ile Ala Ile Ala Trp Met Ser Ala Arg Gln
1               5                   10                  15
Gly Lys Val Ser Tyr Ser Met Asp Tyr Arg Asp Gly Pro Asn Ser Tyr
            20                  25                  30
Asp Cys Ser Ser Ser Val Tyr Tyr Ala Leu Arg Ser Ala Gly Ala Ser
        35                  40                  45
Ser Ala Gly Trp Ala Val Asn Thr Glu Tyr Met His Asp Trp Leu Ile
    50                  55                  60
Lys Asn Gly Tyr Glu Leu Ile Ala Glu Asn Val Asp Trp Asn Ala Val
65                  70                  75                  80
Arg Gly Asp Ile Ala Ile Trp Gly Met Arg Gly His Ser Ser Gly Ala
                85                  90                  95
Gly Gly His Val Val Met Phe Ile Asp Pro Glu Asn Ile Ile His Cys
            100                 105                 110
Asn Trp Ala Asn Asn Gly Ile Thr Val Asn Asn Tyr Asn Gln Thr Ala
        115                 120                 125
Ala Ala Ser Gly Trp Met Tyr Cys Tyr Val Tyr Arg Leu Lys Ser Gly
    130                 135                 140
Ala Ser Thr Gln Gly Lys Ser Leu Leu Glu His His His His His His
145                 150                 155                 160
```

<210> SEQ ID NO 11
<211> LENGTH: 630
<212> TYPE: DNA
<213> ORGANISM: LambdaSa2 phage

<400> SEQUENCE: 11

```
atggaaatca acactgaaat agccattgcc tggatgtctg cacgtcaagg caaggtcagc      60
tattccatgg actaccgtga cggccctaac agctatgact gttccagctc tgtctattat     120
gctctcaggt cagctggtgc aagctcagca ggttgggcgg tcaacactga gtacatgcac     180
gattggctga ttaaaaacgg ttatgagctt attgctgaaa acgtggattg gaatgctgtc     240
cgtggtgata tagcaatttg gggcatgcga gggcactcaa gcggagctgg tggtcatgta     300
gtcatgttta ttgaccctga aaatatcatt cactgtaact gggcaaataa tggcatcaca     360
gtgaacaact acaatcagac agcggctgct agtggctgga tgtattgcta cgtttaccgt     420
ttgaaaagcg gagcttctac ccaaggaaaa agccttgata ccttggtcaa ggaaacccctt    480
gctggtaact acggtaatgg cgaagcacgc aaggcagtgc ttggcaatca atatgaggct     540
gttatgtcag tcatcaatgg caaaactacg actaatcaaa agactgttga ccaacttgtt     600
caactcgagc accaccacca ccaccactga                                      630
```

<210> SEQ ID NO 12
<211> LENGTH: 209
<212> TYPE: PRT
<213> ORGANISM: LambdaSa2 phage

<400> SEQUENCE: 12

```
Met Glu Ile Asn Thr Glu Ile Ala Ile Ala Trp Met Ser Ala Arg Gln
1               5                   10                  15
Gly Lys Val Ser Tyr Ser Met Asp Tyr Arg Asp Gly Pro Asn Ser Tyr
            20                  25                  30
Asp Cys Ser Ser Ser Val Tyr Tyr Ala Leu Arg Ser Ala Gly Ala Ser
```

```
                    35                  40                  45
Ser Ala Gly Trp Ala Val Asn Thr Glu Tyr Met His Asp Trp Leu Ile
 50                  55                  60

Lys Asn Gly Tyr Glu Leu Ile Ala Glu Asn Val Asp Trp Asn Ala Val
 65                  70                  75                  80

Arg Gly Asp Ile Ala Ile Trp Gly Met Arg Gly His Ser Ser Gly Ala
                 85                  90                  95

Gly Gly His Val Val Met Phe Ile Asp Pro Glu Asn Ile Ile His Cys
            100                 105                 110

Asn Trp Ala Asn Asn Gly Ile Thr Val Asn Asn Tyr Asn Gln Thr Ala
        115                 120                 125

Ala Ala Ser Gly Trp Met Tyr Cys Tyr Val Tyr Arg Leu Lys Ser Gly
130                 135                 140

Ala Ser Thr Gln Gly Lys Ser Leu Asp Thr Leu Val Lys Glu Thr Leu
145                 150                 155                 160

Ala Gly Asn Tyr Gly Asn Gly Glu Ala Arg Lys Ala Val Leu Gly Asn
                165                 170                 175

Gln Tyr Glu Ala Val Met Ser Val Ile Asn Gly Lys Thr Thr Thr Asn
            180                 185                 190

Gln Lys Thr Val Asp Gln Leu Val Gln Leu Glu His His His His His
        195                 200                 205

His
```

<210> SEQ ID NO 13
<211> LENGTH: 747
<212> TYPE: DNA
<213> ORGANISM: LambdaSa2 phage

<400> SEQUENCE: 13

```
atggaaatca acactgaaat agccattgcc tggatgtctg cacgtcaagg caaggtcagc    60
tattccatgg actaccgtga cggccctaac agctatgact gttccagctc tgtctattat   120
gctctcaggt cagctggtgc aagctcagca ggttgggcgg tcaacactga gtacatgcac   180
gattggctga ttaaaaacgg ttatgagctt attgctgaaa acgtggattg gaatgctgtc   240
cgtggtgata tagcaatttg gggcatgcga gggcactcaa gcggagctgg tggtcatgta   300
gtcatgttta ttgaccctga aaatatcatt cactgtaact gggcaaataa tggcatcaca   360
gtgaacaact acaatcagac agcggctgct agtggctgga tgtattgcta cgtttaccgt   420
ttgaaaagcg gagcttctac ccaaggaaaa agccttgata ccttggtcaa ggaaaccctt   480
gctggtaact acggtaatgg cgaagcacgc aaggcagtgc ttggcaatca atatgaggct   540
gttatgtcag tcatcaatgg caaaactacg actaatcaaa agactgttga ccaacttgtt   600
caagaggtaa tcgctggcaa acatggcaac ggtgaagctc gtaaaaagtc gcttggtagt   660
caatatgatg cagttcagaa acgagtgacg gaattgctca aaaaacagcc ctctgagccg   720
ctcgagcacc accaccacca ccactga                                        747
```

<210> SEQ ID NO 14
<211> LENGTH: 248
<212> TYPE: PRT
<213> ORGANISM: LambdaSa2 phage

<400> SEQUENCE: 14

```
Met Glu Ile Asn Thr Glu Ile Ala Ile Ala Trp Met Ser Ala Arg Gln
  1               5                  10                  15
```

```
Gly Lys Val Ser Tyr Ser Met Asp Tyr Arg Asp Gly Pro Asn Ser Tyr
            20                  25                  30
Asp Cys Ser Ser Val Tyr Tyr Ala Leu Arg Ser Ala Gly Ala Ser
        35                  40                  45
Ser Ala Gly Trp Ala Val Asn Thr Glu Tyr Met His Asp Trp Leu Ile
50                  55                  60
Lys Asn Gly Tyr Glu Leu Ile Ala Glu Asn Val Asp Trp Asn Ala Val
65                  70                  75                  80
Arg Gly Asp Ile Ala Ile Trp Gly Met Arg Gly His Ser Gly Ala
                85                  90                  95
Gly Gly His Val Val Met Phe Ile Asp Pro Glu Asn Ile Ile His Cys
            100                 105                 110
Asn Trp Ala Asn Asn Gly Ile Thr Val Asn Asn Tyr Asn Gln Thr Ala
            115                 120                 125
Ala Ala Ser Gly Trp Met Tyr Cys Tyr Val Tyr Arg Leu Lys Ser Gly
130                 135                 140
Ala Ser Thr Gln Gly Lys Ser Leu Asp Thr Leu Val Lys Glu Thr Leu
145                 150                 155                 160
Ala Gly Asn Tyr Gly Asn Gly Glu Ala Arg Lys Ala Val Leu Gly Asn
                165                 170                 175
Gln Tyr Glu Ala Val Met Ser Val Ile Asn Gly Lys Thr Thr Thr Asn
            180                 185                 190
Gln Lys Thr Val Asp Gln Leu Val Gln Glu Val Ile Ala Gly Lys His
            195                 200                 205
Gly Asn Gly Glu Ala Arg Lys Lys Ser Leu Gly Ser Gln Tyr Asp Ala
210                 215                 220
Val Gln Lys Arg Val Thr Glu Leu Leu Lys Lys Gln Pro Ser Glu Pro
225                 230                 235                 240
Leu Glu His His His His His His
                245

<210> SEQ ID NO 15
<211> LENGTH: 789
<212> TYPE: DNA
<213> ORGANISM: LambdaSa2 phage

<400> SEQUENCE: 15
atggaaatca acactgaaat agccattgcc tggatgtctg cacgtcaagg caaggtcagc       60
tattccatgg actaccgtga cggccctaac agctatgact gttccagctc tgtctattat      120
gctctcaggt cagctggtgc aagctcagca ggttgggcgg tcaacactga gtacatgcac      180
gattggctga ttaaaaacgg ttatgagctt attgctgaaa acgtggattg gaatgctgtc      240
cgtggtgata tagcaatttg gggcatgcga gggcactcaa gcggagctgg tggtcatgta      300
gtcatgttta ttgaccctga aaatatcatt cactgtaact gggcaaataa tggcatcaca      360
gtgaacaact acaatcagac agcggctgct agtggctgga tgtattgcta cgtttaccgt      420
ttgaaaagcg gagcttctac ccaaggaaaa agccttctcg acacagtaac tccaacgccg      480
aatacaggtt ggaaaacaaa caaatatggc acactatata atcagagtc agctagcttc      540
acacctaata cagatataat aacaagaacg actggtccat ttagaagcat gccgcagtca      600
ggagtcttaa aagcaggtca aacaattcat tatgatgaag tgatgaaaca agacggtcat      660
gtttgggtag ttatacagg taacagtggc aacgtatttt acttgcctgt gagaacatgg      720
cagaagtcta ctaatactct gggtgttctg tggggaacta taaagctcga gcaccaccac      780
``` caccaccac 789

<210> SEQ ID NO 16
<211> LENGTH: 263
<212> TYPE: PRT
<213> ORGANISM: LambdaSa2 phage

<400> SEQUENCE: 16

Met Glu Ile Asn Thr Glu Ile Ala Ile Ala Trp Met Ser Ala Arg Gln
1               5                   10                  15

Gly Lys Val Ser Tyr Ser Met Asp Tyr Arg Asp Gly Pro Asn Ser Tyr
            20                  25                  30

Asp Cys Ser Ser Val Tyr Tyr Ala Leu Arg Ser Ala Gly Ala Ser
        35                  40                  45

Ser Ala Gly Trp Ala Val Asn Thr Glu Tyr Met His Asp Trp Leu Ile
    50                  55                  60

Lys Asn Gly Tyr Glu Leu Ile Ala Glu Asn Val Asp Trp Asn Ala Val
65                  70                  75                  80

Arg Gly Asp Ile Ala Ile Trp Gly Met Arg Gly His Ser Ser Gly Ala
                85                  90                  95

Gly Gly His Val Val Met Phe Ile Asp Pro Glu Asn Ile Ile His Cys
            100                 105                 110

Asn Trp Ala Asn Asn Gly Ile Thr Val Asn Asn Tyr Asn Gln Thr Ala
        115                 120                 125

Ala Ala Ser Gly Trp Met Tyr Cys Tyr Val Tyr Arg Leu Lys Ser Gly
    130                 135                 140

Ala Ser Thr Gln Gly Lys Ser Leu Leu Asp Thr Val Thr Pro Thr Pro
145                 150                 155                 160

Asn Thr Gly Trp Lys Thr Asn Lys Tyr Gly Thr Leu Tyr Lys Ser Glu
                165                 170                 175

Ser Ala Ser Phe Thr Pro Asn Thr Asp Ile Ile Thr Arg Thr Thr Gly
            180                 185                 190

Pro Phe Arg Ser Met Pro Gln Ser Gly Val Leu Lys Ala Gly Gln Thr
        195                 200                 205

Ile His Tyr Asp Glu Val Met Lys Gln Asp Gly His Val Trp Val Gly
    210                 215                 220

Tyr Thr Gly Asn Ser Gly Gln Arg Ile Tyr Leu Pro Val Arg Thr Trp
225                 230                 235                 240

Gln Lys Ser Thr Asn Thr Leu Gly Val Leu Trp Gly Thr Ile Lys Leu
                245                 250                 255

Glu His His His His His
            260

<210> SEQ ID NO 17
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 17

Leu Glu His His His His His His
1               5

<210> SEQ ID NO 18
<211> LENGTH: 6108
<212> TYPE: DNA
<213> ORGANISM: Artificial Sequence
<220> FEATURE:
<223> OTHER INFORMATION: pET21a lysostaphin vector

<400> SEQUENCE: 18

```
tcggtgatgt cggcgatata ggcgccagca accgcacctg tggcgccggt gatgccggcc     60
acgatgcgtc cggcgtagag gatcgagatc tcgatcccgc gaaattaata cgactcacta   120
taggggaatt gtgagcggat aacaattccc ctctagaaat aatttgtttt aactttaaga   180
aggagatata catatggctg caacacatga acattcagca caatggttga ataattacaa   240
aaaaggatat ggttacggcc cttatccatt aggtataaat ggcggtatgc actacggagt   300
tgatttttt atgaatattg aacaccagt aaaagctatt tcaagcggaa aaatagttga   360
agctggttgg agtaattacg gaggaggtaa tcaaataggt cttattgaaa atgatggagt   420
gcatagacaa tggtatatgc atctaagtaa atataatgtt aaagtaggag attatgtcaa   480
agctggtcaa ataatcggtt ggtctggaag cactggttat tctacagcac cacatttaca   540
cttccaaaga atggttaact cattttcaca gtcaactgcc caagatccaa tgcctttctt   600
aaagagcgca ggatatggaa agcaggtgg tacagtaact ccaacgccga atacaggttg   660
gaaaacaaac aaatatggca cactatataa atcagagtca gctagcttca cacctaatac   720
agatataata acaagaacga ctggtccatt tagaagcatg ccgcagtcag gagtcttaaa   780
agcaggtcaa acaattcatt atgatgaagt gatgaaacaa gacggtcatg tttgggtagg   840
ttatacaggt aacagtggcc aacgtattta cttgcctgtg agaacatggc agaagtctac   900
taatactctg ggtgttctgt ggggaactat aaagctcgag caccaccacc accaccactg   960
agatccggct gctaacaaag cccgaaagga agctgagttg gctgctgcca ccgctgagca  1020
ataactagca taaccccttg ggcctctaa acgggtcttg aggggttttt tgctgaaagg  1080
aggaactata tccggattgg cgaatgggac gcgccctgta gcggcgcatt aagcgcggcg  1140
ggtgtggtgg ttacgcgcag cgtgaccgct acacttgcca gcgccctagc gcccgctcct  1200
ttcgctttct tcccttcctt tctcgccacg ttcgccggct ttccccgtca gctctaaat  1260
cggggggctcc ctttagggtt ccgatttagt gctttacggc acctcgaccc caaaaaactt  1320
gattagggtg atggttcacg tagtgggcca tcgccctgat agacggtttt tcgccctttg  1380
acgttggagt ccacgttctt taatagtgga ctcttgttcc aaactggaac aacactcaac  1440
cctatctcgg tctattcttt tgatttataa gggattttgc cgatttcggc ctattggtta  1500
aaaaatgagc tgatttaaca aaaatttaac gcgaattta caaaatatt aacgtttaca  1560
atttcaggtg gcacttttcg gggaaatgtg cgcggaaccc ctatttgttt attttttctaa  1620
atacattcaa atatgtatcc gctcatgaga caataaccct gataaatgct tcaataatat  1680
tgaaaaagga agagtatgag tattcaacat ttccgtgtcg cccttattcc cttttttgcg  1740
gcatttgcc ttcctgtttt tgctcaccca gaaacgctgg tgaaagtaaa agatgctgaa  1800
gatcagttgg gtgcacgagt gggttacatc gaactggatc tcaacagcgg taagatcctt  1860
gagagttttc gccccgaaga acgttttcca atgatgagca cttttaaagt tctgctatgt  1920
ggcgcggtat tatcccgtat tgacgccggg caagagcaac tcggtcgccg catacactat  1980
tctcagaatg acttggttga gtactcacca gtcacagaaa agcatcttac ggatggcatg  2040
acagtaagag aattatgcag tgctgccata accatgagtg ataacactgc ggccaactta  2100
cttctgacaa cgatcggagg accgaaggag ctaaccgctt ttttgcacaa catgggggat  2160
catgtaactc gccttgatcg ttgggaaccg gagctgaatg aagccatacc aaacgacgag  2220
```

-continued

```
cgtgacacca cgatgcctgc agcaatggca acaacgttgc gcaaactatt aactggcgaa      2280
ctacttactc tagcttcccg gcaacaatta atagactgga tggaggcgga taaagttgca      2340
ggaccacttc tgcgctcggc ccttccggct ggctggttta ttgctgataa atctggagcc      2400
ggtgagcgtg ggtctcgcgg tatcattgca gcactgggc cagatggtaa gccctcccgt       2460
atcgtagtta tctacacgac ggggagtcag gcaactatgg atgaacgaaa tagacagatc      2520
gctgagatag gtgcctcact gattaagcat tggtaactgt cagaccaagt ttactcatat      2580
atactttaga ttgatttaaa acttcatttt taatttaaaa ggatctaggt gaagatcctt      2640
tttgataatc tcatgaccaa aatcccttaa cgtgagtttt cgttccactg agcgtcagac      2700
cccgtagaaa agatcaaagg atcttcttga gatccttttt ttctgcgcgt aatctgctgc      2760
ttgcaaacaa aaaaccacc gctaccagcg gtggtttgtt tgccggatca agagctacca       2820 actcttttt cgaaggtaac tggcttcagc agagcgcaga taccaaatac tgtccttcta       2880
gtgtagccgt agttaggcca ccacttcaag aactctgtag caccgcctac atacctcgct      2940
ctgctaatcc tgttaccagt ggctgctgcc agtggcgata gtcgtgtct taccggggttg      3000 gactcaagac gatagttacc ggataaggcg cagcggtcgg gctgaacggg gggttcgtgc      3060
acacagccca gcttggagcg aacgacctac accgaactga gatacctaca gcgtgagcta      3120
tgagaaagcg ccacgcttcc cgaagggaga aaggcggaca ggtatccggt aagcggcagg      3180
gtcggaacag gagagcgcac gagggagctt ccagggggaa acgcctggta tctttatagt      3240
cctgtcgggt ttcgccacct ctgacttgag cgtcgatttt tgtgatgctc gtcagggggg      3300
cggagcctat ggaaaaacgc cagcaacgcg gcctttttac ggttcctggc cttttgctgg      3360
ccttttgctc acatgttctt tcctgcgtta tcccctgatt ctgtggataa ccgtattacc      3420
gcctttgagt gagctgatac cgctcgccgc agccgaacga ccgagcgcag cgagtcagtg      3480
agcgaggaag cggaagagcg cctgatgcgg tattttctcc ttacgcatct gtgcggtatt      3540
tcacaccgca tatatggtgc actctcagta caatctgctc tgatgccgca tagttaagcc      3600
agtatacact ccgctatcgc tacgtgactg ggtcatggct gcgccccgac acccgccaac      3660
acccgctgac gcgccctgac gggcttgtct gctcccggca tccgcttaca gacaagctgt      3720
gaccgtctcc gggagctgca tgtgtcagag gttttcaccg tcatcaccga aacgcgcgag      3780
gcagctgcgg taaagctcat cagcgtggtc gtgaagcgat tcacagatgt ctgcctgttc      3840
atccgcgtcc agctcgttga gtttctccag aagcgttaat gtctggcttc tgataaagcg      3900
ggccatgtta agggcggttt tttcctgttt ggtcactgat gcctccgtgt aagggggatt      3960
tctgttcatg ggggtaatga taccgatgaa acgagagagg atgctcacga tacgggttac      4020
tgatgatgaa catgcccggt tactggaacg ttgtgagggt aaacaactgg cggtatggat      4080
gcggcgggac cagagaaaaa tcactcaggg tcaatgccag cgcttcgtta atacagatgt      4140
aggtgttcca cagggtagcc agcagcatcc tgcgatgcag atccggaaca taatggtgca      4200
gggcgctgac ttccgcgttt ccagacttta cgaaacacgg aaaccgaaga ccattcatgt      4260
tgttgctcag gtcgcagacg ttttgcagca gcagtcgctt cacgttcgct cgcgtatcgg      4320
tgattcattc tgctaaccag taaggcaacc ccgccagcct agccgggtcc tcaacgacag      4380
gagcacgatc atgcgcaccc gtggggccgc catgccggcg ataatggcct gcttctcgcc      4440
gaaacgtttg gtggcgggac cagtgacgaa ggcttgagcg agggcgtgca agattccgaa      4500
taccgcaagc gacaggccga tcatcgtcgc gctccacgca aagcggtcct cgccgaaaat      4560
gacccagagc gctgccggca cctgtcctac gagttgcatg ataaagaaga cagtcataag      4620
```

```
tgcggcgacg atagtcatgc cccgcgccca ccggaaggag ctgactgggt tgaaggctct    4680
caagggcatc ggtcgagatc ccggtgccta atgagtgagc taacttacat taattgcgtt    4740
gcgctcactg cccgctttcc agtcgggaaa cctgtcgtgc cagctgcatt aatgaatcgg    4800
ccaacgcgcg gggagaggcg gtttgcgtat tgggcgccag ggtggttttt cttttcacca    4860
gtgagacggg caacagctga ttgcccttca ccgcctggcc ctgagagagt tgcagcaagc    4920
ggtccacgct ggtttgcccc agcaggcgaa atcctgtttt gatggtggtt aacggcggga    4980
tataacatga gctgtcttcg gtatcgtcgt atcccactac cgagatatcc gcaccaacgc    5040
gcagcccgga ctcggtaatg gcgcgcattg cgcccagcgc catctgatcg ttggcaacca    5100
gcatcgcagt gggaacgatg ccctcattca gcatttgcat ggtttgttga aaaccggaca    5160
tggcactcca gtcgccttcc cgttccgcta tcggctgaat ttgattgcga gtgagatatt    5220
tatgccagcc agccagacgc agacgcgccg agacagaact taatgggccc gctaacagcg    5280
cgatttgctg gtgacccaat gcgaccagat gctccacgcc cagtcgcgta ccgtcttcat    5340
gggagaaaat aatactgttg atgggtgtct ggtcagagac atcaagaaat aacgccggaa    5400
cattagtgca ggcagcttcc acagcaatgg catcctggtc atccagcgga tagttaatga    5460
tcagcccact gacgcgttgc gcgagaagat tgtgcaccgc cgctttacag gcttcgacgc    5520
cgcttcgttc taccatcgac accaccacgc tggcacccag ttgatcggcg cgagatttaa    5580
tcgccgcgac aatttgcgac ggcgcgtgca gggccagact ggaggtggca acgccaatca    5640
gcaacgactg tttgcccgcc agttgttgtg ccacgcggtt gggaatgtaa ttcagctccg    5700
ccatcgccgc ttccactttt tcccgcgttt tcgcagaaac gtggctggcc tggttcacca    5760
cgcgggaaac ggtctgataa gagacaccgg catactctgc gacatcgtat aacgttactg    5820
gtttcacatt caccaccctg aattgactct cttccgggcg ctatcatgcc ataccgcgaa    5880
aggttttgcg ccattcgatg gtgtccggga tctcgacgct ctcccttatg cgactcctgc    5940
attaggaagc agcccagtag taggttgagg ccgttgagca ccgccgccgc aaggaatggt    6000
gcatgcaagg agatggcgcc caacagtccc ccggccacgg ggcctgccac catacccacg    6060
ccgaaacaag cgctcatgag cccgaagtgg cgagcccgat cttcccca                 6108

<210> SEQ ID NO 19
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 19
ggaaaagcag tcgacacagt aactcc                                            26

<210> SEQ ID NO 20
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 20
tagaggcccc aaggggttat g                                                 21
```